(12) United States Patent
Conlon

(10) Patent No.: US 8,157,834 B2
(45) Date of Patent: Apr. 17, 2012

(54) ROTATIONAL COUPLING DEVICE FOR SURGICAL INSTRUMENT WITH FLEXIBLE ACTUATORS

(75) Inventor: Sean P. Conlon, Loveland, OH (US)

(73) Assignee: Ethicon Endo-Surgery, Inc., Cincinnati, OH (US)

(*) Notice: Subject to any disclaimer, the term of this patent is extended or adjusted under 35 U.S.C. 154(b) by 552 days.

(21) Appl. No.: 12/277,957

(22) Filed: Nov. 25, 2008

(65) Prior Publication Data
US 2010/0131005 A1  May 27, 2010

(51) Int. Cl.
*A61B 17/00* (2006.01)

(52) U.S. Cl. .................................... 606/205

(58) Field of Classification Search .......... 606/142, 606/143, 148, 170, 174, 205, 207, 208; 227/175.1, 227/178.1, 180.1
See application file for complete search history.

(56) References Cited

U.S. PATENT DOCUMENTS

| | | |
|---|---|---|
| 645,576 A | 3/1900 | Telsa |
| 649,621 A | 5/1900 | Tesla |
| 787,412 A | 4/1905 | Tesla |
| 1,127,948 A | 2/1915 | Wappler |
| 1,482,653 A | 2/1924 | Lilly |
| 1,625,602 A | 4/1927 | Gould et al. |
| 2,028,635 A | 1/1936 | Wappler |
| 2,113,246 A | 4/1938 | Wappler |
| 2,155,365 A | 4/1939 | Rankin |
| 2,191,858 A | 2/1940 | Moore |
| 2,196,620 A | 4/1940 | Attarian |
| 2,388,137 A | 10/1945 | Graumlich |
| 2,493,108 A | 1/1950 | Casey, Jr. |
| 2,504,152 A | 4/1950 | Riker et al. |
| 2,938,382 A | 5/1960 | De Graaf |
| 2,952,206 A | 9/1960 | Becksted |
| 3,069,195 A | 12/1962 | Buck |
| 3,170,471 A | 2/1965 | Schnitzer |
| 3,435,824 A | 4/1969 | Gamponia |
| 3,470,876 A | 10/1969 | Barchilon |
| 3,669,487 A | 6/1972 | Roberts et al. |
| 3,746,881 A | 7/1973 | Fitch et al. |
| 3,799,672 A | 3/1974 | Vurek |
| 3,854,473 A | 12/1974 | Matsuo |
| 3,946,740 A | 3/1976 | Bassett |
| 3,948,251 A | 4/1976 | Hosono |
| 3,994,301 A | 11/1976 | Agris |
| 4,011,872 A | 3/1977 | Komiya |

(Continued)

FOREIGN PATENT DOCUMENTS

AU   666310 B2   2/1996

(Continued)

OTHER PUBLICATIONS

International Search Report for PCT/US2009/064890, Feb. 3, 2010 (7 pages).

(Continued)

*Primary Examiner* — Ryan Severson
*Assistant Examiner* — Katherine M Shi

(57) ABSTRACT

Rotational couplers for use with surgical devices that are actuated by semi-flexible actuators such as wires and the like. The couplers enable the actuators to apply various actuation motions to actuation features on the surgical device as well as other actuators to apply axial and rotational motions to the surgical device to manipulate the device into various orientations relative to an elongate shaft to which the device is movably attached.

12 Claims, 7 Drawing Sheets

U.S. PATENT DOCUMENTS

| | | | |
|---|---|---|---|
| 4,012,812 A | 3/1977 | Black | |
| 4,164,225 A | 8/1979 | Johnson et al. | |
| 4,178,920 A | 12/1979 | Cawood, Jr. et al. | |
| 4,207,873 A | 6/1980 | Kruy | |
| 4,235,238 A | 11/1980 | Ogiu et al. | |
| 4,258,716 A | 3/1981 | Sutherland | |
| 4,278,077 A | 7/1981 | Mizumoto | |
| 4,285,344 A | 8/1981 | Marshall | |
| 4,311,143 A | 1/1982 | Komiya | |
| 4,329,980 A | 5/1982 | Terada | |
| 4,396,021 A | 8/1983 | Baumgartner | |
| 4,452,246 A | 6/1984 | Bader et al. | |
| 4,461,281 A | 7/1984 | Carson | |
| 4,491,132 A | 1/1985 | Aikins | |
| 4,527,331 A | 7/1985 | Lasner et al. | |
| 4,527,564 A | 7/1985 | Eguchi et al. | |
| 4,538,594 A | 9/1985 | Boebel et al. | |
| D281,104 S | 10/1985 | Davison | |
| 4,569,347 A | 2/1986 | Frisbie | |
| 4,580,551 A | 4/1986 | Siegmund et al. | |
| 4,646,722 A | 3/1987 | Silverstein et al. | |
| 4,653,476 A | 3/1987 | Bonnet | |
| 4,669,470 A | 6/1987 | Brandfield | |
| 4,671,477 A | 6/1987 | Cullen | |
| 4,685,447 A | 8/1987 | Iversen et al. | |
| 4,711,240 A | 12/1987 | Goldwasser et al. | |
| 4,712,545 A | 12/1987 | Honkanen | |
| 4,721,116 A | 1/1988 | Schintgen et al. | |
| 4,733,662 A | 3/1988 | DeSatnick et al. | |
| D295,894 S | 5/1988 | Sharkany et al. | |
| 4,763,669 A | 8/1988 | Jaeger | |
| 4,770,188 A | 9/1988 | Chikama | |
| 4,815,450 A | 3/1989 | Patel | |
| 4,823,794 A | 4/1989 | Pierce | |
| 4,829,999 A | 5/1989 | Auth | |
| 4,873,979 A | 10/1989 | Hanna | |
| 4,880,015 A | 11/1989 | Nierman | |
| 4,911,148 A | 3/1990 | Sosnowski et al. | |
| 4,926,860 A | 5/1990 | Stice et al. | |
| 4,938,214 A | 7/1990 | Specht et al. | |
| 4,950,273 A | 8/1990 | Briggs | |
| 4,950,285 A | 8/1990 | Wilk | |
| 4,960,133 A | 10/1990 | Hewson | |
| 4,977,887 A | 12/1990 | Gouda | |
| 4,984,581 A | 1/1991 | Stice | |
| 5,007,917 A | 4/1991 | Evans | |
| 5,010,876 A | 4/1991 | Henley et al. | |
| 5,020,514 A | 6/1991 | Heckele | |
| 5,020,535 A | 6/1991 | Parker et al. | |
| 5,025,778 A | 6/1991 | Silverstein et al. | |
| 5,033,169 A | 7/1991 | Bindon | |
| 5,037,433 A | 8/1991 | Wilk et al. | |
| 5,041,129 A | 8/1991 | Hayhurst et al. | |
| 5,046,513 A | 9/1991 | Gatturna et al. | |
| 5,050,585 A | 9/1991 | Takahashi | |
| 5,052,372 A | 10/1991 | Shapiro | |
| 5,065,516 A | 11/1991 | Dulebohn | |
| 5,066,295 A | 11/1991 | Kozak et al. | |
| 5,123,913 A | 6/1992 | Wilk et al. | |
| 5,123,914 A | 6/1992 | Cope | |
| 5,133,727 A | 7/1992 | Bales et al. | |
| 5,147,374 A | 9/1992 | Fernandez | |
| 5,174,300 A | 12/1992 | Bales et al. | |
| 5,176,126 A | 1/1993 | Chikama | |
| 5,190,050 A | 3/1993 | Nitzsche | |
| 5,190,555 A | 3/1993 | Wetter et al. | |
| 5,192,284 A | 3/1993 | Pleatman | |
| 5,201,752 A | 4/1993 | Brown et al. | |
| 5,201,908 A | 4/1993 | Jones | |
| 5,203,785 A | 4/1993 | Slater | |
| 5,203,787 A | 4/1993 | Noblitt et al. | |
| 5,209,747 A | 5/1993 | Knoepfler | |
| 5,217,003 A | 6/1993 | Wilk | |
| 5,217,453 A | 6/1993 | Wilk | |
| 5,219,357 A | 6/1993 | Honkanen et al. | |
| 5,219,358 A | 6/1993 | Bendel et al. | |
| 5,222,362 A | 6/1993 | Maus et al. | |
| 5,222,965 A | 6/1993 | Haughton | |
| 5,234,437 A | 8/1993 | Sepetka | |
| 5,234,453 A | 8/1993 | Smith et al. | |
| 5,235,964 A | 8/1993 | Abenaim | |
| 5,242,456 A | 9/1993 | Nash et al. | |
| 5,246,424 A | 9/1993 | Wilk | |
| 5,259,366 A | 11/1993 | Reydel et al. | |
| 5,263,958 A | 11/1993 | deGuillebon et al. | |
| 5,273,524 A | 12/1993 | Fox et al. | |
| 5,275,607 A | 1/1994 | Lo et al. | |
| 5,284,128 A | 2/1994 | Hart | |
| 5,284,162 A | 2/1994 | Wilk | |
| 5,287,845 A | 2/1994 | Faul et al. | |
| 5,290,299 A | 3/1994 | Fain et al. | |
| 5,290,302 A | 3/1994 | Pericic | |
| 5,295,977 A | 3/1994 | Cohen et al. | |
| 5,297,536 A | 3/1994 | Wilk | |
| 5,301,061 A | 4/1994 | Nakada et al. | |
| 5,312,333 A | 5/1994 | Churinetz et al. | |
| 5,312,351 A | 5/1994 | Gerrone | |
| 5,312,416 A | 5/1994 | Spaeth et al. | |
| 5,312,423 A | 5/1994 | Rosenbluth et al. | |
| 5,320,636 A | 6/1994 | Slater | |
| 5,325,845 A | 7/1994 | Adair | |
| 5,330,471 A | 7/1994 | Eggers | |
| 5,330,486 A | 7/1994 | Wilk | |
| 5,330,488 A | 7/1994 | Goldrath | |
| 5,330,496 A | 7/1994 | Alferness | |
| 5,330,502 A | 7/1994 | Hassler et al. | |
| 5,331,971 A | 7/1994 | Bales et al. | |
| 5,334,198 A | 8/1994 | Hart et al. | |
| 5,344,428 A | 9/1994 | Griffiths | |
| 5,350,391 A | 9/1994 | Iacovelli | |
| 5,352,184 A | 10/1994 | Goldberg et al. | |
| 5,352,222 A | 10/1994 | Rydell | |
| 5,354,302 A | 10/1994 | Ko | |
| 5,354,311 A | 10/1994 | Kambin et al. | |
| 5,356,408 A | 10/1994 | Rydell | |
| 5,364,408 A | 11/1994 | Gordon | |
| 5,364,410 A | 11/1994 | Failla et al. | |
| 5,366,466 A | 11/1994 | Christian et al. | |
| 5,366,467 A | 11/1994 | Lynch et al. | |
| 5,368,605 A | 11/1994 | Miller, Jr. | |
| 5,370,647 A | 12/1994 | Graber et al. | |
| 5,370,679 A | 12/1994 | Atlee, III | |
| 5,374,273 A | 12/1994 | Nakao et al. | |
| 5,374,275 A | 12/1994 | Bradley et al. | |
| 5,374,277 A * | 12/1994 | Hassler | 606/207 |
| 5,377,695 A | 1/1995 | An Haack | |
| 5,383,877 A | 1/1995 | Clarke | |
| 5,383,888 A | 1/1995 | Zvenyatsky et al. | |
| 5,391,174 A | 2/1995 | Weston | |
| 5,392,789 A | 2/1995 | Slater et al. | |
| 5,395,386 A | 3/1995 | Slater | |
| 5,401,248 A | 3/1995 | Bencini | |
| 5,403,328 A | 4/1995 | Shallman | |
| 5,403,342 A | 4/1995 | Tovey et al. | |
| 5,403,348 A | 4/1995 | Bonutti | |
| 5,405,073 A | 4/1995 | Porter | |
| 5,405,359 A | 4/1995 | Pierce | |
| 5,409,478 A | 4/1995 | Gerry et al. | |
| 5,417,699 A | 5/1995 | Klein et al. | |
| 5,423,821 A | 6/1995 | Pasque | |
| 5,433,721 A | 7/1995 | Hooven et al. | |
| 5,439,471 A | 8/1995 | Kerr | |
| 5,439,478 A | 8/1995 | Palmer | |
| 5,441,059 A | 8/1995 | Dannan | |
| 5,441,499 A | 8/1995 | Fritzsch | |
| 5,449,021 A | 9/1995 | Chikama | |
| 5,456,667 A | 10/1995 | Ham et al. | |
| 5,456,684 A | 10/1995 | Schmidt et al. | |
| 5,458,131 A | 10/1995 | Wilk | |
| 5,458,583 A | 10/1995 | McNeely et al. | |
| 5,460,168 A | 10/1995 | Masubuchi et al. | |
| 5,460,629 A | 10/1995 | Shlain et al. | |
| 5,462,561 A | 10/1995 | Voda | |
| 5,465,731 A | 11/1995 | Bell et al. | |
| 5,467,763 A | 11/1995 | McMahon et al. | |
| 5,468,250 A | 11/1995 | Paraschac et al. | |
| 5,470,308 A | 11/1995 | Edwards et al. | |

| Patent No. | Date | Inventor |
|---|---|---|
| 5,470,320 A | 11/1995 | Tiefenbrun et al. |
| 5,478,347 A | 12/1995 | Aranyi |
| 5,480,404 A | 1/1996 | Kammerer et al. |
| 5,482,054 A | 1/1996 | Slater et al. |
| 5,484,451 A | 1/1996 | Akopov et al. |
| 5,489,256 A | 2/1996 | Adair |
| 5,496,347 A | 3/1996 | Hashiguchi et al. |
| 5,499,990 A | 3/1996 | Schülken et al. |
| 5,499,992 A | 3/1996 | Meade et al. |
| 5,501,692 A | 3/1996 | Riza |
| 5,503,616 A | 4/1996 | Jones |
| 5,505,686 A | 4/1996 | Willis et al. |
| 5,507,755 A | 4/1996 | Gresl et al. |
| 5,511,564 A | 4/1996 | Wilk |
| 5,514,157 A | 5/1996 | Nicholas et al. |
| 5,522,829 A | 6/1996 | Michalos |
| 5,522,830 A | 6/1996 | Aranyi |
| 5,527,321 A | 6/1996 | Hinchliffe |
| 5,540,648 A | 7/1996 | Yoon |
| 5,554,151 A | 9/1996 | Hinchliffe |
| 5,555,883 A | 9/1996 | Avitall |
| 5,558,133 A | 9/1996 | Bortoli et al. |
| 5,562,693 A | 10/1996 | Devlin et al. |
| 5,569,243 A | 10/1996 | Kortenbach et al. |
| 5,569,298 A | 10/1996 | Schnell |
| 5,573,540 A | 11/1996 | Yoon |
| 5,578,030 A | 11/1996 | Levin |
| 5,582,611 A | 12/1996 | Tsuruta et al. |
| 5,582,617 A | 12/1996 | Klieman et al. |
| 5,584,845 A | 12/1996 | Hart |
| 5,591,179 A | 1/1997 | Edelstein |
| 5,593,420 A | 1/1997 | Eubanks, Jr et al. |
| 5,595,562 A | 1/1997 | Grier |
| 5,597,378 A | 1/1997 | Jervis |
| 5,601,573 A | 2/1997 | Fogelberg et al. |
| 5,601,588 A | 2/1997 | Tonomura et al. |
| 5,604,531 A | 2/1997 | Iddan et al. |
| 5,607,389 A | 3/1997 | Edwards et al. |
| 5,607,450 A | 3/1997 | Zvenyatsky et al. |
| 5,613,975 A | 3/1997 | Christy |
| 5,618,303 A | 4/1997 | Marlow et al. |
| 5,620,415 A | 4/1997 | Lucey et al. |
| 5,624,399 A | 4/1997 | Ackerman |
| 5,624,431 A | 4/1997 | Gerry et al. |
| 5,628,732 A | 5/1997 | Antoon, Jr. et al. |
| 5,630,782 A | 5/1997 | Adair |
| 5,643,283 A | 7/1997 | Younker |
| 5,643,292 A | 7/1997 | Hart |
| 5,643,294 A | 7/1997 | Tovey et al. |
| 5,644,798 A | 7/1997 | Shah |
| 5,645,083 A | 7/1997 | Essig et al. |
| 5,649,372 A | 7/1997 | Souza |
| 5,653,677 A | 8/1997 | Okada et al. |
| 5,653,722 A | 8/1997 | Kieturakis |
| 5,662,663 A | 9/1997 | Shallman |
| 5,669,875 A | 9/1997 | van Eerdenburg |
| 5,681,324 A | 10/1997 | Kammerer et al. |
| 5,681,330 A | 10/1997 | Hughett et al. |
| 5,685,820 A | 11/1997 | Riek et al. |
| 5,690,656 A | 11/1997 | Cope et al. |
| 5,690,660 A | 11/1997 | Kauker et al. |
| 5,695,448 A | 12/1997 | Kimura et al. |
| 5,695,505 A | 12/1997 | Yoon |
| 5,695,511 A | 12/1997 | Cano et al. |
| 5,700,275 A | 12/1997 | Bell et al. |
| 5,702,438 A | 12/1997 | Avitall |
| 5,704,892 A | 1/1998 | Adair |
| 5,709,708 A | 1/1998 | Thal |
| 5,716,326 A | 2/1998 | Dannan |
| 5,730,740 A | 3/1998 | Wales et al. |
| 5,741,278 A | 4/1998 | Stevens |
| 5,741,285 A | 4/1998 | McBrayer et al. |
| 5,746,759 A | 5/1998 | Meade et al. |
| 5,749,881 A | 5/1998 | Sackier et al. |
| 5,749,889 A | 5/1998 | Bacich et al. |
| 5,752,951 A | 5/1998 | Yanik |
| 5,755,731 A | 5/1998 | Grinberg |
| 5,766,167 A | 6/1998 | Eggers et al. |
| 5,766,170 A | 6/1998 | Eggers |
| 5,766,205 A | 6/1998 | Zvenyatsky et al. |
| 5,769,849 A | 6/1998 | Eggers |
| 5,779,701 A | 7/1998 | McBrayer et al. |
| 5,779,716 A | 7/1998 | Cano et al. |
| 5,779,727 A | 7/1998 | Orejola |
| 5,782,859 A | 7/1998 | Nicholas et al. |
| 5,782,866 A | 7/1998 | Wenstrom, Jr. |
| 5,791,022 A | 8/1998 | Bohman |
| 5,792,113 A | 8/1998 | Kramer et al. |
| 5,792,153 A | 8/1998 | Swain et al. |
| 5,792,165 A | 8/1998 | Klieman et al. |
| 5,797,835 A | 8/1998 | Green |
| 5,797,928 A | 8/1998 | Kogasaka |
| 5,797,939 A | 8/1998 | Yoon |
| 5,797,941 A | 8/1998 | Schulze et al. |
| 5,803,903 A | 9/1998 | Athas et al. |
| 5,808,665 A | 9/1998 | Green |
| 5,810,806 A | 9/1998 | Ritchart et al. |
| 5,810,849 A | 9/1998 | Kontos |
| 5,810,865 A | 9/1998 | Koscher et al. |
| 5,810,876 A | 9/1998 | Kelleher |
| 5,810,877 A | 9/1998 | Roth et al. |
| 5,813,976 A | 9/1998 | Filipi et al. |
| 5,814,058 A | 9/1998 | Carlson et al. |
| 5,817,061 A | 10/1998 | Goodwin et al. |
| 5,817,107 A | 10/1998 | Schaller |
| 5,817,119 A | 10/1998 | Klieman et al. |
| 5,819,736 A | 10/1998 | Avny et al. |
| 5,827,281 A | 10/1998 | Levin |
| 5,827,299 A | 10/1998 | Thomason et al. |
| 5,830,231 A | 11/1998 | Geiges, Jr. |
| 5,833,700 A | 11/1998 | Fogelberg et al. |
| 5,833,703 A | 11/1998 | Manushakian |
| 5,843,017 A | 12/1998 | Yoon |
| 5,849,022 A | 12/1998 | Sakashita et al. |
| 5,853,374 A | 12/1998 | Hart et al. |
| 5,855,585 A | 1/1999 | Kontos |
| 5,860,913 A | 1/1999 | Yamaya et al. |
| 5,860,995 A | 1/1999 | Berkelaar |
| 5,868,762 A | 2/1999 | Cragg et al. |
| 5,876,411 A | 3/1999 | Kontos |
| 5,882,331 A | 3/1999 | Sasaki |
| 5,882,344 A | 3/1999 | Stouder, Jr. |
| 5,893,846 A | 4/1999 | Bales et al. |
| 5,893,874 A | 4/1999 | Bourque et al. |
| 5,893,875 A | 4/1999 | O'Connor et al. |
| 5,899,919 A | 5/1999 | Eubanks, Jr. et al. |
| 5,902,254 A | 5/1999 | Magram |
| 5,904,702 A | 5/1999 | Ek et al. |
| 5,908,420 A | 6/1999 | Parins et al. |
| 5,916,147 A | 6/1999 | Boury |
| 5,921,993 A | 7/1999 | Yoon |
| 5,921,997 A | 7/1999 | Fogelberg et al. |
| 5,922,008 A | 7/1999 | Gimpelson |
| 5,925,052 A | 7/1999 | Simmons |
| 5,928,255 A | 7/1999 | Meade et al. |
| 5,928,266 A | 7/1999 | Kontos |
| 5,936,536 A | 8/1999 | Morris |
| 5,944,718 A | 8/1999 | Austin et al. |
| 5,951,549 A | 9/1999 | Richardson et al. |
| 5,954,720 A | 9/1999 | Wilson et al. |
| 5,954,731 A | 9/1999 | Yoon |
| 5,957,943 A | 9/1999 | Vaitekunas |
| 5,957,953 A | 9/1999 | DiPoto et al. |
| 5,971,995 A | 10/1999 | Rousseau |
| 5,976,074 A | 11/1999 | Moriyama |
| 5,976,075 A | 11/1999 | Beane et al. |
| 5,976,130 A | 11/1999 | McBrayer et al. |
| 5,976,131 A | 11/1999 | Guglielmi et al. |
| 5,980,539 A | 11/1999 | Kontos |
| 5,980,556 A | 11/1999 | Giordano et al. |
| 5,984,938 A | 11/1999 | Yoon |
| 5,989,182 A | 11/1999 | Hori et al. |
| 5,993,447 A | 11/1999 | Blewett et al. |
| 5,997,555 A | 12/1999 | Kontos |
| 6,001,120 A | 12/1999 | Levin |
| 6,004,269 A | 12/1999 | Crowley et al. |
| 6,004,330 A | 12/1999 | Middleman et al. |
| 6,007,566 A | 12/1999 | Wenstrom, Jr. |

| | | | |
|---|---|---|---|
| 6,010,515 A | 1/2000 | Swain et al. |
| 6,012,494 A | 1/2000 | Balazs |
| 6,019,770 A | 2/2000 | Christoudias |
| 6,024,708 A | 2/2000 | Bales et al. |
| 6,024,747 A | 2/2000 | Kontos |
| 6,027,522 A | 2/2000 | Palmer |
| 6,030,365 A | 2/2000 | Laufer |
| 6,033,399 A | 3/2000 | Gines |
| 6,053,927 A | 4/2000 | Hamas |
| 6,066,160 A | 5/2000 | Colvin et al. |
| 6,068,603 A | 5/2000 | Suzuki |
| 6,068,629 A | 5/2000 | Haissaguerre et al. |
| 6,071,233 A | 6/2000 | Ishikawa et al. |
| 6,074,408 A | 6/2000 | Freeman |
| 6,086,530 A | 7/2000 | Mack |
| 6,090,108 A | 7/2000 | McBrayer et al. |
| 6,096,046 A | 8/2000 | Weiss |
| 6,102,926 A | 8/2000 | Tartaglia et al. |
| 6,110,154 A | 8/2000 | Shimomura et al. |
| 6,110,183 A | 8/2000 | Cope |
| 6,113,593 A | 9/2000 | Tu et al. |
| 6,117,144 A | 9/2000 | Nobles et al. |
| 6,117,158 A | 9/2000 | Measamer et al. |
| 6,139,555 A | 10/2000 | Hart et al. |
| 6,146,391 A | 11/2000 | Cigaina |
| 6,148,222 A | 11/2000 | Ramsey, III |
| 6,149,653 A | 11/2000 | Deslauriers |
| 6,149,662 A | 11/2000 | Pugliesi et al. |
| 6,159,200 A | 12/2000 | Verdura et al. |
| 6,165,184 A | 12/2000 | Verdura et al. |
| 6,168,570 B1 | 1/2001 | Ferrera |
| 6,168,605 B1 | 1/2001 | Measamer et al. |
| 6,170,130 B1 | 1/2001 | Hamilton et al. |
| 6,179,776 B1 | 1/2001 | Adams et al. |
| 6,179,837 B1 | 1/2001 | Hooven |
| 6,183,420 B1 | 2/2001 | Douk et al. |
| 6,190,353 B1 | 2/2001 | Makower et al. |
| 6,190,384 B1 | 2/2001 | Ouchi |
| 6,190,399 B1 | 2/2001 | Palmer et al. |
| 6,203,533 B1 | 3/2001 | Ouchi |
| 6,206,872 B1 | 3/2001 | Lafond et al. |
| 6,206,877 B1 | 3/2001 | Kese et al. |
| 6,214,007 B1 | 4/2001 | Anderson |
| 6,228,096 B1 | 5/2001 | Marchand |
| 6,245,079 B1 | 6/2001 | Nobles et al. |
| 6,246,914 B1 | 6/2001 | de la Rama et al. |
| 6,258,064 B1 | 7/2001 | Smith et al. |
| 6,261,242 B1 | 7/2001 | Roberts et al. |
| 6,264,664 B1 | 7/2001 | Avellanet |
| 6,270,497 B1 | 8/2001 | Sekino et al. |
| 6,270,505 B1 | 8/2001 | Yoshida et al. |
| 6,277,136 B1 | 8/2001 | Bonutti |
| 6,283,963 B1 | 9/2001 | Regula |
| 6,293,909 B1 | 9/2001 | Chu et al. |
| 6,293,952 B1 | 9/2001 | Brosens et al. |
| 6,296,630 B1 | 10/2001 | Altman et al. |
| 6,322,578 B1 | 11/2001 | Houle et al. |
| 6,326,177 B1 | 12/2001 | Schoenbach et al. |
| 6,328,730 B1 | 12/2001 | Harkrider, Jr. |
| 6,350,267 B1 | 2/2002 | Stefanchik |
| 6,350,278 B1 | 2/2002 | Lenker et al. |
| 6,352,503 B1 | 3/2002 | Matsui et al. |
| 6,352,543 B1 | 3/2002 | Cole |
| 6,355,035 B1 | 3/2002 | Manushakian |
| 6,371,956 B1 | 4/2002 | Wilson et al. |
| 6,379,366 B1 | 4/2002 | Fleischman et al. |
| 6,383,195 B1 | 5/2002 | Richard |
| 6,383,197 B1 | 5/2002 | Conlon et al. |
| 6,391,029 B1 | 5/2002 | Hooven et al. |
| 6,402,735 B1 | 6/2002 | Langevin |
| 6,406,440 B1 | 6/2002 | Stefanchik |
| 6,409,733 B1 | 6/2002 | Conlon et al. |
| 6,431,500 B1 | 8/2002 | Jacobs et al. |
| 6,447,511 B1 | 9/2002 | Slater |
| 6,447,523 B1 | 9/2002 | Middleman et al. |
| 6,454,783 B1 | 9/2002 | Piskun |
| 6,454,785 B2 | 9/2002 | De Hoyos Garza |
| 6,464,701 B1 | 10/2002 | Hooven et al. |
| 6,475,104 B1 | 11/2002 | Lutz et al. |
| 6,485,411 B1 | 11/2002 | Konstorum et al. |
| 6,489,745 B1 | 12/2002 | Koreis |
| 6,491,626 B1 | 12/2002 | Stone et al. |
| 6,491,691 B1 | 12/2002 | Morley et al. |
| 6,493,590 B1 | 12/2002 | Wessman et al. |
| 6,494,893 B2 | 12/2002 | Dubrul et al. |
| 6,503,192 B1 | 1/2003 | Ouchi |
| 6,506,190 B1 | 1/2003 | Walshe |
| 6,508,827 B1 | 1/2003 | Manhes |
| 6,543,456 B1 | 4/2003 | Freeman |
| 6,551,270 B1 | 4/2003 | Bimbo et al. |
| 6,554,829 B2 | 4/2003 | Schulze et al. |
| 6,558,384 B2 | 5/2003 | Mayenberger |
| 6,562,035 B1 | 5/2003 | Levin |
| 6,562,052 B2 | 5/2003 | Nobles et al. |
| 6,569,159 B1 | 5/2003 | Edwards et al. |
| 6,572,629 B2 | 6/2003 | Kalloo et al. |
| 6,572,635 B1 | 6/2003 | Bonutti |
| 6,575,988 B2 | 6/2003 | Rousseau |
| 6,579,311 B1 | 6/2003 | Makower |
| 6,585,642 B2 | 7/2003 | Christopher |
| 6,585,717 B1 | 7/2003 | Wittenberger et al. |
| 6,592,559 B1 | 7/2003 | Pakter et al. |
| 6,592,603 B2 | 7/2003 | Lasner |
| 6,602,262 B2 | 8/2003 | Griego et al. |
| 6,605,105 B1 | 8/2003 | Cuschieri et al. |
| 6,610,072 B1 | 8/2003 | Christy et al. |
| 6,610,074 B2 | 8/2003 | Santilli |
| 6,620,193 B1 | 9/2003 | Lau et al. |
| 6,626,919 B1 | 9/2003 | Swanstrom |
| 6,632,229 B1 | 10/2003 | Yamanouchi |
| 6,638,286 B1 | 10/2003 | Burbank et al. |
| 6,652,521 B2 | 11/2003 | Schulze |
| 6,652,551 B1 | 11/2003 | Heiss |
| 6,656,194 B1 | 12/2003 | Gannoe et al. |
| 6,663,641 B1 | 12/2003 | Kovac et al. |
| 6,666,854 B1 | 12/2003 | Lange |
| 6,672,338 B1 | 1/2004 | Esashi et al. |
| 6,673,058 B2 | 1/2004 | Snow |
| 6,673,087 B1 | 1/2004 | Chang et al. |
| 6,685,628 B2 | 2/2004 | Vu |
| 6,685,724 B1 | 2/2004 | Haluck |
| 6,692,445 B2 | 2/2004 | Roberts et al. |
| 6,699,462 B2 | 2/2004 | Mackenzie et al. |
| 6,699,180 B2 | 3/2004 | Kobayashi |
| 6,699,256 B1 | 3/2004 | Logan et al. |
| 6,699,263 B2 | 3/2004 | Cope |
| 6,706,018 B2 | 3/2004 | Westlund et al. |
| 6,708,066 B2 | 3/2004 | Herbst et al. |
| 6,716,226 B2 | 4/2004 | Sixto, Jr. et al. |
| 6,736,822 B2 | 5/2004 | McClellan et al. |
| 6,740,030 B2 | 5/2004 | Martone et al. |
| 6,743,240 B2 | 6/2004 | Smith et al. |
| 6,749,560 B1 | 6/2004 | Konstorum et al. |
| 6,749,609 B1 | 6/2004 | Lunsford et al. |
| 6,752,768 B2 | 6/2004 | Burdorff et al. |
| 6,752,811 B2 | 6/2004 | Chu et al. |
| 6,752,822 B2 | 6/2004 | Jespersen |
| 6,761,685 B2 | 7/2004 | Adams et al. |
| 6,761,718 B2 | 7/2004 | Madsen |
| 6,761,722 B2 | 7/2004 | Cole et al. |
| 6,773,434 B2 | 8/2004 | Ciarrocca |
| 6,780,151 B2 | 8/2004 | Grabover et al. |
| 6,780,352 B2 | 8/2004 | Jacobson |
| 6,783,491 B2 | 8/2004 | Saadat et al. |
| 6,786,864 B2 | 9/2004 | Matsuura et al. |
| 6,790,173 B2 | 9/2004 | Saadat et al. |
| 6,795,728 B2 | 9/2004 | Chornenky et al. |
| 6,800,056 B2 | 10/2004 | Tartaglia et al. |
| 6,808,491 B2 | 10/2004 | Kortenbach et al. |
| 6,824,548 B2 | 11/2004 | Smith et al. |
| 6,837,847 B2 | 1/2005 | Ewers et al. |
| 6,843,794 B2 | 1/2005 | Sixto, Jr. et al. |
| 6,861,250 B1 | 3/2005 | Cole et al. |
| 6,866,627 B2 | 3/2005 | Nozue |
| 6,878,106 B1 | 4/2005 | Herrmann |
| 6,878,110 B2 | 4/2005 | Yang et al. |
| 6,884,213 B2 | 4/2005 | Raz et al. |
| 6,887,255 B2 | 5/2005 | Shimm |

| | | |
|---|---|---|
| 6,896,683 B1 | 5/2005 | Gadberry et al. |
| 6,908,427 B2 | 6/2005 | Fleener et al. |
| 6,908,476 B2 | 6/2005 | Jud et al. |
| 6,916,284 B2 | 7/2005 | Moriyama |
| 6,918,871 B2 | 7/2005 | Schulze |
| 6,926,725 B2 | 8/2005 | Cooke et al. |
| 6,932,810 B2 | 8/2005 | Ryan |
| 6,932,824 B1 | 8/2005 | Roop et al. |
| 6,932,827 B2 | 8/2005 | Cole |
| 6,932,834 B2 | 8/2005 | Lizardi et al. |
| 6,939,327 B2 | 9/2005 | Hall et al. |
| 6,942,613 B2 | 9/2005 | Ewers et al. |
| 6,945,472 B2 | 9/2005 | Wuttke et al. |
| 6,945,979 B2 | 9/2005 | Kortenbach et al. |
| 6,955,683 B2 | 10/2005 | Bonutti |
| 6,958,035 B2 | 10/2005 | Friedman et al. |
| 6,960,162 B2 | 11/2005 | Saadat et al. |
| 6,960,163 B2 | 11/2005 | Ewers et al. |
| 6,962,587 B2 | 11/2005 | Johnson et al. |
| 6,964,662 B2 | 11/2005 | Kidooka |
| 6,966,909 B2 | 11/2005 | Marshall et al. |
| 6,966,919 B2 | 11/2005 | Sixto, Jr. et al. |
| 6,967,462 B1 | 11/2005 | Landis |
| 6,971,988 B2 | 12/2005 | Orban, III |
| 6,972,017 B2 | 12/2005 | Smith et al. |
| 6,974,411 B2 | 12/2005 | Belson |
| 6,976,992 B2 | 12/2005 | Sachatello et al. |
| 6,984,203 B2 | 1/2006 | Tartaglia et al. |
| 6,984,205 B2 | 1/2006 | Gazdzinski |
| 6,986,774 B2 | 1/2006 | Middleman et al. |
| 6,988,987 B2 | 1/2006 | Ishikawa et al. |
| 6,989,028 B2 | 1/2006 | Lashinski et al. |
| 6,991,627 B2 | 1/2006 | Madhani et al. |
| 6,994,708 B2 | 2/2006 | Manzo |
| 6,997,931 B2 | 2/2006 | Sauer et al. |
| 7,000,818 B2 | 2/2006 | Shelton, IV et al. |
| 7,008,375 B2 | 3/2006 | Weisel |
| 7,009,634 B2 | 3/2006 | Iddan et al. |
| 7,010,340 B2 | 3/2006 | Scarantino et al. |
| 7,020,531 B1 | 3/2006 | Colliou et al. |
| 7,025,580 B2 | 4/2006 | Heagy et al. |
| 7,029,435 B2 | 4/2006 | Nakao |
| 7,029,438 B2 | 4/2006 | Morin et al. |
| 7,035,680 B2 | 4/2006 | Partridge et al. |
| 7,037,290 B2 | 5/2006 | Gardeski et al. |
| 7,041,052 B2 | 5/2006 | Saadat et al. |
| 7,052,489 B2 | 5/2006 | Griego et al. |
| 7,060,024 B2 | 6/2006 | Long et al. |
| 7,060,025 B2 | 6/2006 | Long et al. |
| 7,063,697 B2 | 6/2006 | Slater |
| 7,063,715 B2 | 6/2006 | Onuki et al. |
| 7,066,879 B2 | 6/2006 | Fowler et al. |
| 7,066,936 B2 | 6/2006 | Ryan |
| 7,070,602 B2 | 7/2006 | Smith et al. |
| 7,076,305 B2 | 7/2006 | Imran et al. |
| 7,083,629 B2 | 8/2006 | Weller et al. |
| 7,087,071 B2 | 8/2006 | Nicholas et al. |
| 7,090,673 B2 | 8/2006 | Dycus et al. |
| 7,090,685 B2 | 8/2006 | Kortenbach et al. |
| 7,093,518 B2 | 8/2006 | Gmeilbauer |
| 7,101,371 B2 | 9/2006 | Dycus et al. |
| 7,101,372 B2 | 9/2006 | Dycus et al. |
| 7,101,373 B2 | 9/2006 | Dycus et al. |
| 7,105,000 B2 | 9/2006 | McBrayer |
| 7,105,005 B2 | 9/2006 | Blake |
| 7,108,703 B2 | 9/2006 | Danitz et al. |
| 7,112,208 B2 | 9/2006 | Morris et al. |
| 7,115,092 B2 | 10/2006 | Park et al. |
| 7,118,531 B2 | 10/2006 | Krill |
| 7,118,578 B2 | 10/2006 | West, Jr. et al. |
| 7,118,587 B2 | 10/2006 | Dycus et al. |
| 7,128,708 B2 | 10/2006 | Saadat et al. |
| RE39,415 E | 11/2006 | Bales et al. |
| 7,131,978 B2 | 11/2006 | Sancoff et al. |
| 7,131,979 B2 | 11/2006 | DiCarlo et al. |
| 7,131,980 B1 | 11/2006 | Field et al. |
| 7,137,980 B2 | 11/2006 | Buysse et al. |
| 7,137,981 B2 | 11/2006 | Long |
| 7,146,984 B2 | 12/2006 | Stack et al. |
| 7,147,650 B2 | 12/2006 | Lee |
| 7,153,321 B2 | 12/2006 | Andrews |
| 7,163,525 B2 | 1/2007 | Franer |
| 7,172,714 B2 | 2/2007 | Jacobson |
| 7,179,254 B2 | 2/2007 | Pendekanti et al. |
| 7,195,612 B2 | 3/2007 | Van Sloten et al. |
| 7,195,631 B2 | 3/2007 | Dumbauld |
| 7,208,005 B2 | 4/2007 | Frecker et al. |
| 7,211,092 B2 | 5/2007 | Hughett |
| 7,223,272 B2 | 5/2007 | Francere et al. |
| 7,232,414 B2 | 6/2007 | Gonzalez |
| 7,232,445 B2 | 6/2007 | Kortenbach et al. |
| 7,241,290 B2 | 7/2007 | Doyle et al. |
| 7,244,228 B2 | 7/2007 | Lubowski |
| 7,252,660 B2 | 8/2007 | Kunz |
| 7,270,663 B2 | 9/2007 | Nakao |
| 7,294,139 B1 | 11/2007 | Gengler |
| 7,301,250 B2 | 11/2007 | Cassel |
| 7,306,597 B2 | 12/2007 | Manzo |
| 7,318,802 B2 | 1/2008 | Suzuki et al. |
| 7,320,695 B2 | 1/2008 | Carroll |
| 7,322,934 B2 | 1/2008 | Miyake et al. |
| 7,323,006 B2 | 1/2008 | Andreas et al. |
| 7,329,257 B2 | 2/2008 | Kanehira et al. |
| 7,329,383 B2 | 2/2008 | Stinson |
| 7,344,536 B1 | 3/2008 | Lunsford et al. |
| 7,352,387 B2 | 4/2008 | Yamamoto |
| 7,364,582 B2 | 4/2008 | Lee |
| 7,371,215 B2 | 5/2008 | Colliou et al. |
| 7,381,216 B2 | 6/2008 | Buzzard et al. |
| 7,393,322 B2 | 7/2008 | Wenchell |
| 7,402,162 B2 | 7/2008 | Ouchi |
| 7,404,791 B2 | 7/2008 | Linares et al. |
| 7,413,563 B2 | 8/2008 | Corcoran et al. |
| 7,416,554 B2 | 8/2008 | Lam et al. |
| 7,422,590 B2 | 9/2008 | Kupferschmid et al. |
| 7,435,257 B2 | 10/2008 | Lashinski et al. |
| 7,452,327 B2 | 11/2008 | Durgin et al. |
| 7,455,208 B2 | 11/2008 | Wales et al. |
| 7,468,066 B2 | 12/2008 | Vargas et al. |
| 7,488,295 B2 | 2/2009 | Burbank et al. |
| 7,497,867 B2 | 3/2009 | Lasner et al. |
| 7,507,200 B2 | 3/2009 | Okada |
| 7,524,281 B2 | 4/2009 | Chu et al. |
| 7,524,302 B2 | 4/2009 | Tower |
| 7,534,228 B2 | 5/2009 | Williams |
| 7,544,203 B2 | 6/2009 | Chin et al. |
| 7,548,040 B2 | 6/2009 | Lee et al. |
| 7,549,564 B2 | 6/2009 | Boudreaux |
| 7,553,278 B2 | 6/2009 | Kucklick |
| 7,553,298 B2 | 6/2009 | Hunt et al. |
| 7,559,887 B2 | 7/2009 | Dannan |
| 7,560,006 B2 | 7/2009 | Rakos et al. |
| 7,561,916 B2 | 7/2009 | Hunt et al. |
| 7,566,334 B2 | 7/2009 | Christian et al. |
| 7,579,550 B2 | 8/2009 | Dayton et al. |
| 7,582,096 B2 | 9/2009 | Gellman et al. |
| 7,588,557 B2 | 9/2009 | Nakao |
| 7,618,398 B2 | 11/2009 | Holman et al. |
| 7,632,250 B2 | 12/2009 | Smith et al. |
| 7,635,373 B2 | 12/2009 | Ortiz |
| 7,637,903 B2 | 12/2009 | Lentz et al. |
| 7,651,483 B2 | 1/2010 | Byrum et al. |
| 7,651,509 B2 | 1/2010 | Bojarski et al. |
| 7,654,431 B2 | 2/2010 | Hueil et al. |
| 7,662,089 B2 | 2/2010 | Okada et al. |
| 7,666,180 B2 | 2/2010 | Holsten et al. |
| 7,713,270 B2 | 5/2010 | Suzuki |
| 7,736,374 B2 | 6/2010 | Vaughan et al. |
| 7,762,998 B2 | 7/2010 | Birk et al. |
| 7,771,416 B2 | 8/2010 | Spivey et al. |
| 7,780,683 B2 | 8/2010 | Roue et al. |
| 7,794,475 B2 | 9/2010 | Hess et al. |
| 7,837,615 B2 | 11/2010 | Le et al. |
| 7,850,660 B2 | 12/2010 | Uth et al. |
| 7,857,183 B2 | 12/2010 | Shelton, IV |
| 7,862,546 B2 | 1/2011 | Conlon et al. |
| 7,867,216 B2 | 1/2011 | Wahr et al. |
| 7,896,887 B2 | 3/2011 | Rimbaugh et al. |

| Patent/Publication | Date | Inventor |
|---|---|---|
| 7,918,869 B2 | 4/2011 | Saadat et al. |
| 7,931,624 B2 | 4/2011 | Smith et al. |
| 7,947,000 B2 | 5/2011 | Vargas et al. |
| 7,955,298 B2 | 6/2011 | Carroll et al. |
| 7,963,975 B2 | 6/2011 | Criscuolo |
| 2001/0049497 A1 | 12/2001 | Kalloo et al. |
| 2002/0022771 A1 | 2/2002 | Diokno et al. |
| 2002/0022857 A1 | 2/2002 | Goldsteen et al. |
| 2002/0023353 A1 | 2/2002 | Ting-Kung |
| 2002/0042562 A1 | 4/2002 | Meron et al. |
| 2002/0049439 A1 | 4/2002 | Mulier et al. |
| 2002/0068945 A1 | 6/2002 | Sixto, Jr. et al. |
| 2002/0078967 A1 | 6/2002 | Sixto, Jr. et al. |
| 2002/0082516 A1 | 6/2002 | Stefanchik |
| 2002/0095164 A1 | 7/2002 | Andreas et al. |
| 2002/0107530 A1 | 8/2002 | Sauer et al. |
| 2002/0133115 A1 | 9/2002 | Gordon et al. |
| 2002/0138086 A1 | 9/2002 | Sixto, Jr. et al. |
| 2002/0147456 A1 | 10/2002 | Diduch et al. |
| 2002/0183591 A1 | 12/2002 | Matsuura et al. |
| 2003/0023255 A1 | 1/2003 | Miles et al. |
| 2003/0036679 A1 | 2/2003 | Kortenbach et al. |
| 2003/0069602 A1 | 4/2003 | Jacobs et al. |
| 2003/0083681 A1 | 5/2003 | Moutafis et al. |
| 2003/0114732 A1 | 6/2003 | Webler et al. |
| 2003/0120257 A1 | 6/2003 | Houston et al. |
| 2003/0130564 A1 | 7/2003 | Martone et al. |
| 2003/0130656 A1 | 7/2003 | Levin |
| 2003/0158521 A1 | 8/2003 | Ameri |
| 2003/0167062 A1 | 9/2003 | Gambale et al. |
| 2003/0171651 A1 | 9/2003 | Page et al. |
| 2003/0176880 A1 | 9/2003 | Long et al. |
| 2003/0216611 A1 | 11/2003 | Vu |
| 2003/0216615 A1 | 11/2003 | Ouchi |
| 2003/0220545 A1 | 11/2003 | Ouchi |
| 2003/0225312 A1 | 12/2003 | Suzuki et al. |
| 2003/0225332 A1 | 12/2003 | Okada et al. |
| 2003/0229269 A1 | 12/2003 | Humphrey |
| 2003/0229371 A1 | 12/2003 | Whitworth |
| 2003/0236549 A1 | 12/2003 | Bonadio et al. |
| 2004/0002683 A1 | 1/2004 | Nicholson et al. |
| 2004/0034369 A1 | 2/2004 | Sauer et al. |
| 2004/0098007 A1 | 5/2004 | Heiss |
| 2004/0101456 A1 | 5/2004 | Kuroshima et al. |
| 2004/0116948 A1 | 6/2004 | Sixto, Jr. et al. |
| 2004/0133077 A1 | 7/2004 | Obenchain et al. |
| 2004/0133089 A1 | 7/2004 | Kilcoyne et al. |
| 2004/0136779 A1 | 7/2004 | Bhaskar |
| 2004/0138525 A1 | 7/2004 | Saadat et al. |
| 2004/0138529 A1 | 7/2004 | Wiltshire et al. |
| 2004/0138587 A1 | 7/2004 | Lyons, IV |
| 2004/0186350 A1 | 9/2004 | Brenneman et al. |
| 2004/0193009 A1 | 9/2004 | Jaffe et al. |
| 2004/0193146 A1 | 9/2004 | Lee et al. |
| 2004/0193186 A1 | 9/2004 | Kortenbach et al. |
| 2004/0193188 A1 | 9/2004 | Francese |
| 2004/0193189 A1 | 9/2004 | Kortenbach et al. |
| 2004/0193200 A1 | 9/2004 | Dworschak et al. |
| 2004/0199052 A1 | 10/2004 | Banik et al. |
| 2004/0210245 A1 | 10/2004 | Erickson et al. |
| 2004/0215058 A1 | 10/2004 | Zirps et al. |
| 2004/0225183 A1 | 11/2004 | Michlitsch et al. |
| 2004/0225186 A1 | 11/2004 | Horne, Jr. et al. |
| 2004/0230095 A1 | 11/2004 | Stefanchik et al. |
| 2004/0230096 A1 | 11/2004 | Stefanchik et al. |
| 2004/0230097 A1 | 11/2004 | Stefanchik et al. |
| 2004/0230161 A1 | 11/2004 | Zeiner |
| 2004/0249246 A1 | 12/2004 | Campos |
| 2004/0249367 A1 | 12/2004 | Saadat et al. |
| 2004/0249394 A1 | 12/2004 | Morris et al. |
| 2004/0249443 A1 | 12/2004 | Shanley et al. |
| 2005/0004515 A1 | 1/2005 | Hart et al. |
| 2005/0033265 A1 | 2/2005 | Engel et al. |
| 2005/0033277 A1 | 2/2005 | Clague et al. |
| 2005/0033319 A1 | 2/2005 | Gambale et al. |
| 2005/0033333 A1 | 2/2005 | Smith et al. |
| 2005/0043690 A1 | 2/2005 | Todd |
| 2005/0049616 A1 | 3/2005 | Rivera et al. |
| 2005/0065397 A1 | 3/2005 | Saadat et al. |
| 2005/0065517 A1 | 3/2005 | Chin |
| 2005/0070754 A1 | 3/2005 | Nobis et al. |
| 2005/0070763 A1 | 3/2005 | Nobis et al. |
| 2005/0070764 A1 | 3/2005 | Nobis et al. |
| 2005/0080413 A1 | 4/2005 | Canady |
| 2005/0085693 A1 | 4/2005 | Belson et al. |
| 2005/0085832 A1 | 4/2005 | Sancoff et al. |
| 2005/0090837 A1 | 4/2005 | Sixto, Jr. et al. |
| 2005/0090838 A1 | 4/2005 | Sixto, Jr. et al. |
| 2005/0101837 A1 | 5/2005 | Kalloo et al. |
| 2005/0101838 A1 | 5/2005 | Camillocci et al. |
| 2005/0107663 A1 | 5/2005 | Saadat et al. |
| 2005/0107664 A1 | 5/2005 | Kalloo et al. |
| 2005/0110881 A1 | 5/2005 | Glukhovsky et al. |
| 2005/0113847 A1 | 5/2005 | Gadberry et al. |
| 2005/0124855 A1 | 6/2005 | Jaffe et al. |
| 2005/0125010 A1 | 6/2005 | Smith et al. |
| 2005/0131279 A1 | 6/2005 | Boulais et al. |
| 2005/0131457 A1 | 6/2005 | Douglas et al. |
| 2005/0137454 A1 | 6/2005 | Saadat et al. |
| 2005/0143647 A1 | 6/2005 | Minai et al. |
| 2005/0143690 A1 | 6/2005 | High |
| 2005/0143774 A1 | 6/2005 | Polo |
| 2005/0143803 A1 | 6/2005 | Watson et al. |
| 2005/0149087 A1 | 7/2005 | Ahlberg et al. |
| 2005/0149096 A1 | 7/2005 | Hilal et al. |
| 2005/0159648 A1 | 7/2005 | Freed |
| 2005/0165272 A1 | 7/2005 | Okada et al. |
| 2005/0165378 A1 | 7/2005 | Heinrich et al. |
| 2005/0165411 A1 | 7/2005 | Orban, III |
| 2005/0165429 A1 | 7/2005 | Douglas et al. |
| 2005/0182429 A1 | 8/2005 | Yamanouchi |
| 2005/0192478 A1 | 9/2005 | Williams et al. |
| 2005/0192598 A1 | 9/2005 | Johnson et al. |
| 2005/0192602 A1 | 9/2005 | Manzo |
| 2005/0192654 A1 | 9/2005 | Chanduszko et al. |
| 2005/0209624 A1 | 9/2005 | Vijay |
| 2005/0215858 A1 | 9/2005 | Vail, III |
| 2005/0216050 A1 | 9/2005 | Sepetka et al. |
| 2005/0228406 A1 | 10/2005 | Bose |
| 2005/0234297 A1 | 10/2005 | Devierre et al. |
| 2005/0250983 A1 | 11/2005 | Tremaglio et al. |
| 2005/0250990 A1 | 11/2005 | Le et al. |
| 2005/0250993 A1 | 11/2005 | Jaeger |
| 2005/0251166 A1 | 11/2005 | Vaughan et al. |
| 2005/0251176 A1 | 11/2005 | Swanstrom et al. |
| 2005/0261674 A1 | 11/2005 | Nobis et al. |
| 2005/0267492 A1 | 12/2005 | Poncet et al. |
| 2005/0272975 A1 | 12/2005 | McWeeney et al. |
| 2005/0272977 A1 | 12/2005 | Saadat et al. |
| 2005/0273084 A1 | 12/2005 | Hinman et al. |
| 2005/0277945 A1 | 12/2005 | Saadat et al. |
| 2005/0277951 A1 | 12/2005 | Smith et al. |
| 2005/0277952 A1 | 12/2005 | Arp et al. |
| 2005/0277954 A1 | 12/2005 | Smith et al. |
| 2005/0277955 A1 | 12/2005 | Palmer et al. |
| 2005/0277956 A1 | 12/2005 | Francese et al. |
| 2005/0277957 A1 | 12/2005 | Kuhns et al. |
| 2005/0283118 A1 | 12/2005 | Uth et al. |
| 2005/0283119 A1 | 12/2005 | Uth et al. |
| 2005/0288555 A1 | 12/2005 | Binmoeller |
| 2006/0004406 A1 | 1/2006 | Wehrstein et al. |
| 2006/0004409 A1 | 1/2006 | Nobis et al. |
| 2006/0004410 A1 | 1/2006 | Nobis et al. |
| 2006/0015009 A1 | 1/2006 | Jaffe et al. |
| 2006/0016853 A1* | 1/2006 | Racenet .................. 227/176.1 |
| 2006/0020167 A1 | 1/2006 | Sitzmann |
| 2006/0020247 A1 | 1/2006 | Kagan et al. |
| 2006/0025654 A1 | 2/2006 | Suzuki et al. |
| 2006/0025781 A1 | 2/2006 | Young et al. |
| 2006/0025812 A1 | 2/2006 | Shelton, IV |
| 2006/0025819 A1 | 2/2006 | Nobis et al. |
| 2006/0036267 A1 | 2/2006 | Saadat et al. |
| 2006/0041188 A1 | 2/2006 | Dirusso et al. |
| 2006/0058582 A1 | 3/2006 | Maahs et al. |
| 2006/0058776 A1 | 3/2006 | Bilsbury |
| 2006/0069396 A1 | 3/2006 | Meade et al. |
| 2006/0069424 A1 | 3/2006 | Acosta et al. |
| 2006/0074413 A1 | 4/2006 | Behzadian |

| | | | | | | |
|---|---|---|---|---|---|---|
| 2006/0079890 A1 | 4/2006 | Guerra | 2007/0088370 A1 | 4/2007 | Kahle et al. | |
| 2006/0089528 A1 | 4/2006 | Tartaglia et al. | 2007/0100375 A1 | 5/2007 | Mikkaichi et al. | |
| 2006/0095060 A1 | 5/2006 | Mayenberger et al. | 2007/0100376 A1 | 5/2007 | Mikkaichi et al. | |
| 2006/0100687 A1 | 5/2006 | Fahey et al. | 2007/0106118 A1 | 5/2007 | Moriyama | |
| 2006/0106423 A1 | 5/2006 | Weisel et al. | 2007/0112251 A1 | 5/2007 | Nakhuda | |
| 2006/0111209 A1 | 5/2006 | Hinman et al. | 2007/0112331 A1 | 5/2007 | Weber et al. | |
| 2006/0111210 A1 | 5/2006 | Hinman et al. | 2007/0112342 A1 | 5/2007 | Pearson et al. | |
| 2006/0111704 A1 | 5/2006 | Brenneman et al. | 2007/0112383 A1 | 5/2007 | Conlon et al. | |
| 2006/0129166 A1 | 6/2006 | Lavelle | 2007/0112384 A1 | 5/2007 | Conlon et al. | |
| 2006/0135962 A1 | 6/2006 | Kick et al. | 2007/0112385 A1 | 5/2007 | Conlon | |
| 2006/0135971 A1 | 6/2006 | Swanstrom et al. | 2007/0112417 A1 | 5/2007 | Shanley et al. | |
| 2006/0135984 A1 | 6/2006 | Kramer et al. | 2007/0112425 A1 | 5/2007 | Schaller et al. | |
| 2006/0142644 A1 | 6/2006 | Mulac et al. | 2007/0118115 A1 | 5/2007 | Artale et al. | |
| 2006/0142652 A1 | 6/2006 | Keenan | 2007/0123840 A1 | 5/2007 | Cox | |
| 2006/0142790 A1 | 6/2006 | Gertner | 2007/0129605 A1 | 6/2007 | Schaaf | |
| 2006/0142798 A1 | 6/2006 | Holman et al. | 2007/0129719 A1 | 6/2007 | Kendale et al. | |
| 2006/0149132 A1 | 7/2006 | Iddan | 2007/0129760 A1 | 6/2007 | Demarais et al. | |
| 2006/0149135 A1 | 7/2006 | Paz | 2007/0135709 A1 | 6/2007 | Rioux et al. | |
| 2006/0161190 A1 | 7/2006 | Gadberry et al. | 2007/0142706 A1 | 6/2007 | Matsui et al. | |
| 2006/0167416 A1 | 7/2006 | Mathis et al. | 2007/0156127 A1 | 7/2007 | Rioux et al. | |
| 2006/0167482 A1 | 7/2006 | Swain et al. | 2007/0161855 A1 | 7/2007 | Mikkaichi et al. | |
| 2006/0178560 A1 | 8/2006 | Saadat et al. | 2007/0173691 A1 | 7/2007 | Yokoi et al. | |
| 2006/0183975 A1 | 8/2006 | Saadat et al. | 2007/0173869 A1 | 7/2007 | Gannoe et al. | |
| 2006/0184161 A1 | 8/2006 | Maahs et al. | 2007/0173870 A2 | 7/2007 | Zacharias | |
| 2006/0189844 A1 | 8/2006 | Tien | 2007/0173872 A1 | 7/2007 | Neuenfeldt | |
| 2006/0189845 A1 | 8/2006 | Maahs et al. | 2007/0175947 A1* | 8/2007 | Ortiz et al. | 227/175.1 |
| 2006/0190027 A1 | 8/2006 | Downey | 2007/0179525 A1 | 8/2007 | Frecker et al. | |
| 2006/0195084 A1 | 8/2006 | Slater | 2007/0179530 A1 | 8/2007 | Tieu et al. | |
| 2006/0200005 A1 | 9/2006 | Bjork et al. | 2007/0197865 A1 | 8/2007 | Miyake et al. | |
| 2006/0200169 A1 | 9/2006 | Sniffin | 2007/0198057 A1 | 8/2007 | Gelbart et al. | |
| 2006/0200170 A1 | 9/2006 | Aranyi | 2007/0203487 A1 | 8/2007 | Sugita | |
| 2006/0200199 A1 | 9/2006 | Bonutti et al. | 2007/0208364 A1 | 9/2007 | Smith et al. | |
| 2006/0217665 A1 | 9/2006 | Prosek | 2007/0213754 A1 | 9/2007 | Mikkaichi et al. | |
| 2006/0217697 A1 | 9/2006 | Lau et al. | 2007/0225554 A1 | 9/2007 | Maseda et al. | |
| 2006/0217742 A1 | 9/2006 | Messerly et al. | 2007/0233040 A1 | 10/2007 | Macnamara et al. | |
| 2006/0217743 A1 | 9/2006 | Messerly et al. | 2007/0244358 A1 | 10/2007 | Lee | |
| 2006/0229639 A1 | 10/2006 | Whitfield | 2007/0250057 A1 | 10/2007 | Nobis et al. | |
| 2006/0229640 A1 | 10/2006 | Whitfield | 2007/0255096 A1 | 11/2007 | Stefanchik et al. | |
| 2006/0237022 A1 | 10/2006 | Chen et al. | 2007/0255100 A1 | 11/2007 | Barlow et al. | |
| 2006/0237023 A1 | 10/2006 | Cox et al. | 2007/0255273 A1 | 11/2007 | Fernandez et al. | |
| 2006/0241570 A1 | 10/2006 | Wilk | 2007/0255303 A1 | 11/2007 | Bakos et al. | |
| 2006/0247576 A1 | 11/2006 | Poncet | 2007/0255306 A1 | 11/2007 | Conlon et al. | |
| 2006/0247673 A1 | 11/2006 | Voegele et al. | 2007/0260112 A1 | 11/2007 | Rahmani | |
| 2006/0253004 A1 | 11/2006 | Frisch et al. | 2007/0260117 A1 | 11/2007 | Zwolinski et al. | |
| 2006/0253039 A1 | 11/2006 | McKenna et al. | 2007/0260121 A1 | 11/2007 | Bakos et al. | |
| 2006/0258907 A1 | 11/2006 | Stefanchik et al. | 2007/0260273 A1 | 11/2007 | Cropper et al. | |
| 2006/0258908 A1 | 11/2006 | Stefanchik et al. | 2007/0270629 A1 | 11/2007 | Charles | |
| 2006/0258910 A1 | 11/2006 | Stefanchik et al. | 2007/0270889 A1 | 11/2007 | Conlon et al. | |
| 2006/0258954 A1 | 11/2006 | Timberlake et al. | 2007/0270895 A1 | 11/2007 | Nobis et al. | |
| 2006/0258955 A1 | 11/2006 | Hoffman et al. | 2007/0270907 A1 | 11/2007 | Stokes et al. | |
| 2006/0259010 A1 | 11/2006 | Stefanchik et al. | 2007/0282371 A1 | 12/2007 | Lee et al. | |
| 2006/0264752 A1 | 11/2006 | Rubinsky et al. | 2007/0299387 A1 | 12/2007 | Williams et al. | |
| 2006/0264904 A1 | 11/2006 | Kerby et al. | 2008/0004650 A1 | 1/2008 | George | |
| 2006/0264930 A1 | 11/2006 | Nishimura | 2008/0015409 A1 | 1/2008 | Barlow et al. | |
| 2006/0270902 A1 | 11/2006 | Igarashi et al. | 2008/0015552 A1 | 1/2008 | Doyle et al. | |
| 2006/0271102 A1 | 11/2006 | Bosshard et al. | 2008/0027387 A1 | 1/2008 | Grabinsky | |
| 2006/0276835 A1 | 12/2006 | Uchida | 2008/0033451 A1 | 2/2008 | Rieber et al. | |
| 2006/0281970 A1 | 12/2006 | Stokes et al. | 2008/0051629 A1 | 2/2008 | Sugiyama et al. | |
| 2006/0282106 A1 | 12/2006 | Cole et al. | 2008/0051735 A1 | 2/2008 | Measamer et al. | |
| 2006/0285732 A1 | 12/2006 | Horn et al. | 2008/0058586 A1 | 3/2008 | Karpiel | |
| 2006/0287644 A1 | 12/2006 | Inganas et al. | 2008/0065169 A1 | 3/2008 | Colliou et al. | |
| 2006/0287666 A1 | 12/2006 | Saadat et al. | 2008/0086172 A1 | 4/2008 | Martin et al. | |
| 2006/0293626 A1 | 12/2006 | Byrum et al. | 2008/0097472 A1 | 4/2008 | Agmon et al. | |
| 2007/0002135 A1 | 1/2007 | Glukhovsky | 2008/0097483 A1 | 4/2008 | Ortiz et al. | |
| 2007/0005019 A1 | 1/2007 | Okishige | 2008/0103527 A1 | 5/2008 | Martin et al. | |
| 2007/0015965 A1 | 1/2007 | Cox et al. | 2008/0114384 A1 | 5/2008 | Chang et al. | |
| 2007/0016225 A1 | 1/2007 | Nakao | 2008/0119870 A1 | 5/2008 | Williams | |
| 2007/0032700 A1 | 2/2007 | Fowler et al. | 2008/0125796 A1 | 5/2008 | Graham | |
| 2007/0032701 A1 | 2/2007 | Fowler et al. | 2008/0132892 A1 | 6/2008 | Lunsford et al. | |
| 2007/0043261 A1 | 2/2007 | Watanabe et al. | 2008/0139882 A1 | 6/2008 | Fujimori | |
| 2007/0043345 A1 | 2/2007 | Davalos et al. | 2008/0147113 A1 | 6/2008 | Nobis et al. | |
| 2007/0049800 A1 | 3/2007 | Boulais | 2008/0171907 A1 | 7/2008 | Long et al. | |
| 2007/0049902 A1 | 3/2007 | Griffin et al. | 2008/0188868 A1 | 8/2008 | Weitzner et al. | |
| 2007/0051375 A1 | 3/2007 | Milliman | 2008/0200755 A1 | 8/2008 | Bakos | |
| 2007/0060880 A1 | 3/2007 | Gregorich et al. | 2008/0200762 A1 | 8/2008 | Stokes et al. | |
| 2007/0067017 A1 | 3/2007 | Trapp | 2008/0200911 A1 | 8/2008 | Long | |
| 2007/0073102 A1 | 3/2007 | Matsuno et al. | 2008/0200912 A1 | 8/2008 | Long | |
| 2007/0073269 A1 | 3/2007 | Becker | 2008/0200933 A1 | 8/2008 | Bakos et al. | |
| 2007/0079924 A1 | 4/2007 | Saadat et al. | 2008/0200934 A1 | 8/2008 | Fox | |

| | | |
|---|---|---|
| 2008/0208213 A1 | 8/2008 | Benjamin et al. |
| 2008/0221587 A1 | 9/2008 | Schwartz |
| 2008/0221619 A1 | 9/2008 | Spivey et al. |
| 2008/0228213 A1 | 9/2008 | Blakeney et al. |
| 2008/0230972 A1 | 9/2008 | Ganley |
| 2008/0234696 A1 | 9/2008 | Taylor et al. |
| 2008/0243106 A1 | 10/2008 | Coe et al. |
| 2008/0243148 A1 | 10/2008 | Mikkaichi et al. |
| 2008/0243176 A1 | 10/2008 | Weitzner et al. |
| 2008/0262540 A1 | 10/2008 | Bangera et al. |
| 2008/0269782 A1 | 10/2008 | Stefanchik et al. |
| 2008/0269783 A1 | 10/2008 | Griffith |
| 2008/0275474 A1 | 11/2008 | Martin et al. |
| 2008/0275475 A1 | 11/2008 | Schwemberger et al. |
| 2008/0287737 A1 | 11/2008 | Dejima |
| 2008/0287983 A1 | 11/2008 | Smith et al. |
| 2008/0300461 A1 | 12/2008 | Shaw et al. |
| 2008/0300547 A1 | 12/2008 | Bakos |
| 2008/0309758 A1 | 12/2008 | Karasawa et al. |
| 2008/0312496 A1 | 12/2008 | Zwolinski |
| 2008/0312499 A1 | 12/2008 | Handa et al. |
| 2008/0312500 A1 | 12/2008 | Asada et al. |
| 2008/0312506 A1 | 12/2008 | Spivey et al. |
| 2008/0319436 A1 | 12/2008 | Daniel et al. |
| 2008/0319439 A1 | 12/2008 | Ootsubu |
| 2009/0054728 A1 | 2/2009 | Trusty |
| 2009/0062788 A1 | 3/2009 | Long et al. |
| 2009/0062792 A1 | 3/2009 | Vakharia et al. |
| 2009/0062795 A1 | 3/2009 | Vakharia et al. |
| 2009/0069634 A1 | 3/2009 | Larkin |
| 2009/0076499 A1 | 3/2009 | Azure |
| 2009/0082776 A1 | 3/2009 | Cresina |
| 2009/0082779 A1 | 3/2009 | Nakao |
| 2009/0112059 A1 | 4/2009 | Nobis |
| 2009/0112062 A1 | 4/2009 | Bakos |
| 2009/0112063 A1 | 4/2009 | Bakos et al. |
| 2009/0131751 A1 | 5/2009 | Spivey et al. |
| 2009/0131932 A1 | 5/2009 | Vakharia et al. |
| 2009/0131933 A1 | 5/2009 | Ghabrial et al. |
| 2009/0143639 A1 | 6/2009 | Stark |
| 2009/0143649 A1 | 6/2009 | Rossi |
| 2009/0143794 A1 | 6/2009 | Conlon et al. |
| 2009/0149710 A1 | 6/2009 | Stefanchik et al. |
| 2009/0177031 A1 | 7/2009 | Surti et al. |
| 2009/0177219 A1 | 7/2009 | Conlon |
| 2009/0182332 A1 | 7/2009 | Long et al. |
| 2009/0192344 A1 | 7/2009 | Bakos et al. |
| 2009/0198231 A1 | 8/2009 | Esser et al. |
| 2009/0227828 A1 | 9/2009 | Swain et al. |
| 2009/0248055 A1 | 10/2009 | Spivey et al. |
| 2009/0281559 A1 | 11/2009 | Swain et al. |
| 2009/0287236 A1 | 11/2009 | Bakos et al. |
| 2009/0292164 A1 | 11/2009 | Yamatani |
| 2009/0299135 A1 | 12/2009 | Spivey |
| 2009/0299143 A1 | 12/2009 | Conlon et al. |
| 2009/0299362 A1 | 12/2009 | Long et al. |
| 2009/0299385 A1 | 12/2009 | Stefanchik et al. |
| 2009/0299406 A1 | 12/2009 | Swain et al. |
| 2009/0299409 A1 | 12/2009 | Coe et al. |
| 2009/0306658 A1 | 12/2009 | Nobis et al. |
| 2009/0306683 A1 | 12/2009 | Zwolinski et al. |
| 2009/0322864 A1 | 12/2009 | Karasawa et al. |
| 2009/0326561 A1 | 12/2009 | Carroll, II et al. |
| 2010/0010294 A1 | 1/2010 | Conlon et al. |
| 2010/0010298 A1 | 1/2010 | Bakos et al. |
| 2010/0010299 A1 | 1/2010 | Bakos et al. |
| 2010/0010303 A1 | 1/2010 | Bakos |
| 2010/0010510 A1 | 1/2010 | Stefanchik |
| 2010/0010511 A1 | 1/2010 | Harris et al. |
| 2010/0023032 A1 | 1/2010 | Granja Filho |
| 2010/0042045 A1 | 2/2010 | Spivey |
| 2010/0048990 A1 | 2/2010 | Bakos |
| 2010/0049190 A1 | 2/2010 | Long et al. |
| 2010/0049223 A1 | 2/2010 | Granja Filho |
| 2010/0056861 A1 | 3/2010 | Spivey |
| 2010/0056862 A1 | 3/2010 | Bakos |
| 2010/0057085 A1 | 3/2010 | Holcomb et al. |
| 2010/0057108 A1 | 3/2010 | Spivey et al. |
| 2010/0063538 A1 | 3/2010 | Spivey et al. |
| 2010/0076451 A1 | 3/2010 | Zwolinski et al. |
| 2010/0081877 A1 | 4/2010 | Vakharia |
| 2010/0087813 A1 | 4/2010 | Long |
| 2010/0113872 A1 | 5/2010 | Asada et al. |
| 2010/0121362 A1 | 5/2010 | Clague et al. |
| 2010/0130817 A1 | 5/2010 | Conlon |
| 2010/0130975 A1 | 5/2010 | Long |
| 2010/0152539 A1 | 6/2010 | Ghabrial et al. |
| 2010/0152609 A1 | 6/2010 | Zwolinski et al. |
| 2010/0152746 A1 | 6/2010 | Ceniccola et al. |
| 2010/0179510 A1 | 7/2010 | Fox et al. |
| 2010/0179530 A1 | 7/2010 | Long et al. |
| 2010/0191050 A1 | 7/2010 | Zwolinski |
| 2010/0191267 A1 | 7/2010 | Fox |
| 2010/0198005 A1 | 8/2010 | Fox |
| 2010/0198149 A1 | 8/2010 | Fox |
| 2010/0198244 A1 | 8/2010 | Spivey et al. |
| 2010/0198248 A1 | 8/2010 | Vakharia |
| 2010/0249700 A1 | 9/2010 | Spivey |
| 2010/0286791 A1 | 11/2010 | Goldsmith |
| 2010/0298642 A1 | 11/2010 | Trusty et al. |
| 2010/0312056 A1 | 12/2010 | Galperin et al. |
| 2010/0331622 A2 | 12/2010 | Conlon |
| 2010/0331774 A2 | 12/2010 | Spivey |
| 2011/0093009 A1 | 4/2011 | Fox |
| 2011/0098694 A1 | 4/2011 | Long |
| 2011/0098704 A1 | 4/2011 | Long et al. |
| 2011/0105850 A1 | 5/2011 | Voegele et al. |
| 2011/0112434 A1 | 5/2011 | Ghabrial et al. |
| 2011/0115891 A1 | 5/2011 | Trusty |
| 2011/0124964 A1 | 5/2011 | Nobis |
| 2011/0152609 A1 | 6/2011 | Trusty et al. |
| 2011/0152610 A1 | 6/2011 | Trusty et al. |
| 2011/0152612 A1 | 6/2011 | Trusty et al. |
| 2011/0152858 A1 | 6/2011 | Long et al. |
| 2011/0152859 A1 | 6/2011 | Long et al. |
| 2011/0152878 A1 | 6/2011 | Trusty et al. |
| 2011/0152923 A1 | 6/2011 | Fox |
| 2011/0160514 A1 | 6/2011 | Long et al. |
| 2011/0190659 A1 | 8/2011 | Long et al. |
| 2011/0190764 A1 | 8/2011 | Long et al. |

FOREIGN PATENT DOCUMENTS

| | | |
|---|---|---|
| DE | 3008120 A1 | 9/1980 |
| DE | 4323585 A1 | 1/1995 |
| DE | 19757056 B4 | 8/2008 |
| DE | 102006027873 B4 | 10/2009 |
| EP | 0086338 A1 | 8/1983 |
| EP | 0286415 A2 | 10/1988 |
| EP | 0589454 A2 | 3/1994 |
| EP | 0464479 B1 | 3/1995 |
| EP | 0529675 B1 | 2/1996 |
| EP | 0724863 B1 | 7/1999 |
| EP | 0760629 B1 | 11/1999 |
| EP | 0818974 B1 | 11/1999 |
| EP | 1281356 A2 | 2/2003 |
| EP | 0947166 B1 | 5/2003 |
| EP | 0836832 B1 | 12/2003 |
| EP | 1402837 A1 | 3/2004 |
| EP | 0744918 B1 | 4/2004 |
| EP | 0931515 B1 | 8/2004 |
| EP | 1411843 B1 | 10/2004 |
| EP | 1150614 B1 | 11/2004 |
| EP | 1477104 A1 | 11/2004 |
| EP | 1481642 A1 | 12/2004 |
| EP | 1493391 A1 | 1/2005 |
| EP | 0848598 B1 | 2/2005 |
| EP | 1281360 B1 | 3/2005 |
| EP | 1568330 A1 | 8/2005 |
| EP | 1452143 B1 | 9/2005 |
| EP | 1616527 A2 | 1/2006 |
| EP | 1006888 B1 | 3/2006 |
| EP | 1629764 A1 | 3/2006 |
| EP | 1013229 B1 | 6/2006 |
| EP | 1721561 A1 | 11/2006 |
| EP | 1153578 B1 | 3/2007 |
| EP | 1334696 B1 | 3/2007 |
| EP | 1769766 A1 | 4/2007 |
| EP | 1836971 A2 | 9/2007 |

| | | | |
|---|---|---|---|
| EP | 1836980 A1 | 9/2007 |
| EP | 1854421 A2 | 11/2007 |
| EP | 1857061 A1 | 11/2007 |
| EP | 1875876 A1 | 1/2008 |
| EP | 1891881 A1 | 2/2008 |
| EP | 1902663 A1 | 3/2008 |
| EP | 1477106 B1 | 6/2008 |
| EP | 1949844 A1 | 7/2008 |
| EP | 1518499 B1 | 8/2008 |
| EP | 1709918 B1 | 10/2008 |
| EP | 1985226 A2 | 10/2008 |
| EP | 1994904 A1 | 11/2008 |
| EP | 1707130 B1 | 12/2008 |
| EP | 1769749 B1 | 11/2009 |
| FR | 2731610 A1 | 9/1996 |
| GB | 330629 A | 6/1930 |
| GB | 2335860 A | 10/1999 |
| GB | 2403909 A | 1/2005 |
| GB | 2421190 A | 6/2006 |
| GB | 2443261 A | 4/2008 |
| JP | 56-46674 | 4/1981 |
| JP | 8-29699 A | 2/1996 |
| JP | 2002-369791 A | 12/2002 |
| JP | 2003-088494 A | 3/2003 |
| JP | 2003-235852 A | 8/2003 |
| JP | 2004-33525 A | 2/2004 |
| JP | 2004-065745 A | 3/2004 |
| JP | 2005-121947 A | 5/2005 |
| JP | 2005-261514 A | 9/2005 |
| NL | 1021295 C2 | 2/2004 |
| SU | 194230 | 5/1967 |
| SU | 980703 | 12/1982 |
| WO | WO 84/01707 A1 | 5/1984 |
| WO | WO 92/13494 A1 | 8/1992 |
| WO | WO 93/10850 A1 | 6/1993 |
| WO | WO 93/20760 A1 | 10/1993 |
| WO | WO 93/20765 A1 | 10/1993 |
| WO | WO 95/09666 A1 | 4/1995 |
| WO | WO 96/22056 A1 | 7/1996 |
| WO | WO 96/27331 A1 | 9/1996 |
| WO | WO 96/39946 A1 | 12/1996 |
| WO | WO 97/12557 A1 | 4/1997 |
| WO | WO 98/01080 A1 | 1/1998 |
| WO | WO 99/09919 A1 | 3/1999 |
| WO | WO 99/17661 A1 | 4/1999 |
| WO | WO 99/30622 A2 | 6/1999 |
| WO | WO 00/35358 A1 | 6/2000 |
| WO | WO 01/10319 A1 | 2/2001 |
| WO | WO 01/41627 A2 | 6/2001 |
| WO | WO 01/58360 A2 | 8/2001 |
| WO | WO 02/11621 A1 | 2/2002 |
| WO | WO 02/34122 A2 | 5/2002 |
| WO | WO 02/094082 A2 | 11/2002 |
| WO | WO 03/045260 A1 | 6/2003 |
| WO | WO 03/047684 A2 | 6/2003 |
| WO | WO 03/059412 A2 | 7/2003 |
| WO | WO 03/078721 A2 | 9/2003 |
| WO | WO 03/082129 A2 | 10/2003 |
| WO | WO 2004/006789 A1 | 1/2004 |
| WO | WO 2004/028613 A2 | 4/2004 |
| WO | WO 2004/037123 A1 | 5/2004 |
| WO | WO 2004/052221 A1 | 6/2004 |
| WO | WO 2004/086984 A1 | 10/2004 |
| WO | WO 2005/009211 A2 | 2/2005 |
| WO | WO 2005/018467 A2 | 3/2005 |
| WO | WO 2005/037088 A2 | 4/2005 |
| WO | WO 2005/048827 A1 | 6/2005 |
| WO | WO 2005/065284 A2 | 7/2005 |
| WO | WO 2005/097019 A2 | 10/2005 |
| WO | WO 2005/097234 A2 | 10/2005 |
| WO | WO 2005/112810 A2 | 12/2005 |
| WO | WO 2005/120363 A1 | 12/2005 |
| WO | WO 2006/007399 A1 | 1/2006 |
| WO | WO 2006/041881 A2 | 4/2006 |
| WO | WO 2006/060405 A2 | 6/2006 |
| WO | WO 2006/110733 A2 | 10/2006 |
| WO | WO 2006/113216 A2 | 10/2006 |
| WO | WO 2007/014063 A2 | 2/2007 |
| WO | WO 2007/048085 A2 | 4/2007 |
| WO | WO 2007/063550 A2 | 6/2007 |
| WO | WO 2007/100067 A1 | 9/2007 |
| WO | WO 2007/109171 A2 | 9/2007 |
| WO | WO 2008/005433 A1 | 1/2008 |
| WO | WO 2008/041225 A2 | 4/2008 |
| WO | WO 2008/076337 A1 | 6/2008 |
| WO | WO 2008/076800 A2 | 6/2008 |
| WO | WO 2008/101075 A2 | 8/2008 |
| WO | WO 2008/102154 A2 | 8/2008 |
| WO | WO 2009/021030 A1 | 2/2009 |
| WO | WO 2009/027065 A1 | 3/2009 |
| WO | WO 2009/029065 A1 | 3/2009 |
| WO | WO 2009/032623 A2 | 3/2009 |
| WO | WO 2009/121017 A1 | 10/2009 |
| WO | WO 2010/027688 A1 | 3/2010 |
| WO | WO 2010/080974 A1 | 7/2010 |
| WO | WO 2010/088481 A1 | 8/2010 |

OTHER PUBLICATIONS

D. Wilhelm et al., "An Innovative, Safe and Sterile Sigmoid Access (ISSA) for Notes," Endoscopy 2007, vol. 39, pp. 401-406.

Nakazawa et al., "Radiofrequency Ablation of Hepatocellular Carcinoma: Correlation Between Local Tumor Progression After Ablation and Ablative Margin," AJR, 188, pp. 480-488 (Feb. 2007).

Miklavčič et al., "A validated model of in vivo electric field distribution in tissues for electrochemotherapy and for DNA electrotransfer for gene therapy," Biochimica et Biophysica Acta, 1523, pp. 73-83 (2000).

Evans, "Ablative and cathether-delivered therapies for colorectal liver metastases (CRLM)," EJSO, 33, pp. S64-S75 (2007).

Wong et al., "Combined Percutaneous Radiofrequency Ablation and Ethanol Injection for Hepatocellular Carcinoma in High-Risk Locations," AJR, 190, pp. W187-W195 (2008).

Heller et al., "Electrically mediated plasmid DNA delivery to hepatocellular carcinomas in vivo," Gene Therapy, 7, pp. 826-829 (2000).

Widera et al., "Increased DNA Vaccine Delivery and Immunogenicity by Electroporation In Vivo," The Journal of Immunology, 164, pp. 4635-4640 (2000).

Weaver et al., "Theory of electroporation: A review," Bioelectrochemistry and Bioenergetics, 41, pp. 135-160 (1996).

Mulier et al., "Radiofrequency Ablation Versus Resection for Resectable Colorectal Liver Metastases: Time for a Randomized Trial?" Annals of Surgical Oncology, 15(1), pp. 144-157 (2008).

Link et al., "Regional Chemotherapy of Nonresectable Colorectal Liver Metastases with Mitoxanthrone, 5-Fluorouracil, Folinic Acid, and Mitomycin C May Prolong Survival," Cancer, 92, pp. 2746-2753 (2001).

Guyton et al., "Membrane Potentials and Action Potentials," W.B. Sanders, ed. Textbook of Medical Physiology, p. 56 (2000).

Guyton et al., "Contraction of Skeletal Muscle," Textbook of Medical Physiology, pp. 82-84 (2000).

"Ethicon Endo-Surgery Novel Investigational Notes and SSL Devices Featured in 15 Presentations at Sages," Apr. 22, 2009 Press Release; URL http://www.jnj.com/connect/news/all/20090422_152000; accessed Aug. 28, 2009 (3 pages).

"Ethicon Endo-Surgery Studies Presented At DDW Demonstrate Potential of Pure Notes Surgery With Company's Toolbox," Jun. 3, 2009 Press Release; URL http://www.jnj.com/connect/news/product/20090603_120000; accessed Aug. 28, 2009 (3 pages).

Castellvi et al., "Hybrid Transvaginal Notes Sleeve Gastrectomy in a Porcine Model Using a Magnetically Anchored Camera and Novel Instrumentation," Abstract submitted along with Poster at SAGES Annual Meeting in Phoenix, AZ, Apr. 22, 2009 (1 page).

Castellvi et al., "Hybrid Transvaginal Notes Sleeve Gastrectomy in a Porcine Model Using a Magnetically Anchored Camera and Novel Instrumentation," Poster submitted along with Abstract at SAGES Annual Meeting in Phoenix, AZ, Apr. 22, 2009 (1 page).

OCTO Port Modular Laparoscopy System for Single Incision Access, Jan. 4, 2010; URL http://www.medgadget.com/archives/2010/01/octo_port_modular_laparo...; accessed Jan. 5, 2010 (4 pages).

Hakko Retractors, obtained Aug. 25, 2009 (5 pages).

Zadno et al., "Linear Superelasticity in Cold-Worked NI-TI," Engineering Aspects of Shape Memory Alloys, pp. 414-419.
U.S. Appl. No. 12/607,252, filed Oct. 28, 2009.
U.S. Appl. No. 12/580,400, filed Oct. 16, 2009.
U.S. Appl. No. 12/607,388, filed Oct. 28, 2009.
U.S. Appl. No. 12/612,911, filed Nov. 5, 2009.
U.S. Appl. No. 12/614,143, filed Nov. 6, 2009.
U.S. Appl. No. 12/617,998, filed Nov. 13, 2009.
U.S. Appl. No. 12/640,440, filed Dec. 17, 2009.
U.S. Appl. No. 12/640,469, filed Dec. 17, 2009.
U.S. Appl. No. 12/640,476, filed Dec. 17, 2009.
U.S. Appl. No. 12/640,492, filed Dec. 17, 2009.
U.S. Appl. No. 12/641,823, filed Dec. 18, 2009.
U.S. Appl. No. 12/641,853, filed Dec. 18, 2009.
U.S. Appl. No. 12/641,837, filed Dec. 18, 2009.
U.S. Appl. No. 12/651,181, filed Dec. 31, 2009.
U.S. Appl. No. 12/696,598, filed Jan. 29, 2010.
U.S. Appl. No. 12/696,626, filed Jan. 29, 2010.
U.S. Appl. No. 12/694,452, filed Jan. 27, 2010.
U.S. Appl. No. 12/752,701, filed Apr. 1, 2010.
Michael S. Kavic, M.D., "Natural Orifice Translumenal Endoscopic Surgery: "Notes"", JSLS, vol. 10, pp. 133-134 (2006).
Ethicon, Inc., "Wound Closure Manual: Chapter 3 (The Surgical Needle)," 15 pages, (publication date unknown).
Guido M. Sclabas, M.D., et al., "Endoluminal Methods for Gastrotomy Closure in Natural Orifice TransEnteric Surgery (Notes)," Surgical Innovation, vol. 13, No. 1, pp. 23-30, Mar. 2006.
Fritscher-Ravens, et al., "Transgastric Gastropexy and Hiatal Hernia Repair for GERD Under EUS Control: a Porcine Model," Gastrointestinal Endoscopy, vol. 59, No. 1, pp. 89-95, 2004.
Ogando, "Prototype Tools That Go With the Flow," Design News, 2 pages, Jul. 17, 2006.
Edd, et al., "In Vivo Results of a New Focal Tissue Ablation Technique: Irreversible Electroporation," IEEE Trans Biomed Eng, vol. 53, pp. 1409-1415, 2006.
Kennedy, et al., "High-Burst-Strength, Feedback-Controlled Bipolar Vessel Sealing," Surgical Endoscopy, vol. 12, pp. 876-878 (1998).
Collins et al., "Local Gene Therapy of Solid Tumors with GM-GSF and B7-1 Eradicates Both Treated and Distal Tumors," Cancer Gene Therapy, vol. 13, pp. 1061-1071 (2006).
K. Sumiyama et al., "Transesophageal Mediastinoscopy by Submucosal Endoscopy With Mucosal Flap Safety Value Technique," Gastrointest Endosc., Apr. 2007, vol. 65(4), pp. 679-683 (Abstract).
K. Sumiyama et al., "Submucosal Endoscopy with Mucosal Flap Safety Valve," Gastrointest Endosc. Apr. 2007, vol. 65(4) pp. 694-695 (Abstract).
K. Sumiyama et al., "Transgastric Cholecystectomy: Transgastric Accessibility to the Gallbladder Improved with the SEMF Method and a Novel Multibending Therapeutic Endoscope," Gastrointest Endosc., Jun. 2007, vol. 65(7), pp. 1028-1034 (Abstract).
K. Sumiyama et al., "Endoscopic Caps," Tech. Gastrointest. Endosc., vol. 8, pp. 28-32, 2006.
"Z-Offset Technique Used in the Introduction of Trocar During Laparoscopic Surgery," M.S. Hershey Notes Presentation to EES Notes Development Team, Sep. 27, 2007.
F.N. Denans, Nouveau Procede Pour La Guerison Des Plaies Des Intestines. Extrait Des Seances De La Societe Royale De Medecine De Marseille, Pendant Le Mois De Decembre 1825, et le Premier Tremestre De 1826, Séance Du 24 Fevrier 1826. Recueil De La Societe Royale De Medecin De Marseille. Marseille: Impr. D'Achard, 1826; 1:127-31. (with English translation).
I. Fraser, "An Historical Perspective on Mechanical Aids in Intestinal Anastomosis," Surg. Gynecol. Obstet. (Oct. 1982), vol. 155, pp. 566-574.
M.E. Ryan et al., "Endoscopic Intervention for Biliary Leaks After Laparoscopic Cholecystectomy: A Multicenter Review," Gastrointest. Endosc., vol. 47(3), 1998, pp. 261-266.
C. Cope, "Creation of Compression Gastroenterostomy by Means of the Oral, Percutaneous, or Surgical Introduction of Magnets: Feasibility Study in Swine," J. Vasc Interv Radiol, (1995), vol. 6(4), pp. 539-545.
J.W. Hazey et al., "Natural Orifice Transgastric Endoscopic Peritoneoscopy in Humans: Initial Clinical Trial," Surg Endosc, (Jan. 2008), vol. 22(1), pp. 16-20.
N. Chopita et al., "Endoscopic Gastroenteric Anastamosis Using Magnets," Endoscopy, (2005), vol. 37(4), pp. 313-317.
C. Cope et al., "Long Term Patency of Experimental Magnetic Compression Gastroenteric Anastomoses Achieved with Covered Stents," Gastrointest Endosc, (2001), vol. 53, pp. 780-784.
H. Okajima et al., "Magnet Compression Anastamosis for Bile Duct Stenosis After Duct to Duct Biliary Reconstruction in Living Donor Liver Transplantation," Liver Transplantation (2005), pp. 473-475.
A. Fritscher-Ravens et al., "Transluminal Endosurgery: Single Lumen Access Anastamotic Device for Flexible Endoscopy," Gastrointestinal Endosc, (2003), vol. 58(4), pp. 585-591.
G.A. Hallenbeck, M.D. et al., "An Instrument for Colorectal Anastomosis Without Sutrues," Dis Col Rectum, (1963), vol. 5, pp. 98-101.
T. Hardy, Jr., M.D. et al., "A Biofragmentable Ring for Sutureless Bowel Anastomosis. An Experimental Study," Dis Col Rectum, (1985), vol. 28, pp. 484-490.
P. O'Neill, M.D. et al., "Nonsuture Intestinal Anastomosis," Am J. Surg, (1962), vol. 104, pp. 761-767.
C.P. Swain, M.D. et al., "Anastomosis at Flexible Endoscopy: An Experimental Study of Compression Button Gastrojejunostomy," Gastrointest Endosc, (1991), vol. 37, pp. 628-632.
J.B. Murphy, M.D., "Cholecysto-Intestinal, Gastro-Intestinal, Entero-Intestinal Anastomosis, and Approximation Without Sutures (original research)," Med Rec, (Dec. 10, 1892), vol. 42(24), pp. 665-676.
USGI® EndoSurgical Operating System—g-Prox® Tissue Grasper/Approximation Device; [online] URL: http://www.usgimedical.com/eos/components-gprox.htm—accessed May 30, 2008 (2 pages).
Printout of web page—http://www.vacumed.com/zcom/product/Product.do?compid=27&prodid=852, #51XX Low-Cost Permanent Tubes 2MM ID, Smooth Interior Walls, VacuMed, Ventura, California, Accessed Jul. 24, 2007.
Endoscopic Retrograde Cholangiopancreatogram (ERCP); [online] URL: http://www.webmd.com/digestive-disorders/endoscopic-retrograde-cholangiopancreatogram-ercp.htm; last updated: Apr. 30, 2007; accessed: Feb. 21, 2008 (6 pages).
ERCP; Jackson Siegelbaum Gastroenterology; [online] URL: http://www.gicare.com/pated/epdgs20.htm; accessed Feb. 21, 2008 (3 pages).
D.G. Fong et al., "Transcolonic Ventral Wall Hernia Mesh Fixation in a Porcine Model," Endoscopy 2007; 39: 865-869.
B. Rubinsky, Ph.D., "Irreversible Electroporation in Medicine," Technology in Cancer Research and Treatment, vol. 6, No. 4, Aug. 2007, pp. 255-259.
D.B. Nelson, MD et al., "Endoscopic Hemostatic Devices," Gastrointestinal Endoscopy, vol. 54, No. 6, 2001, pp. 833-840.
CRE™ Pulmonary Balloon Dilator; [online] URL: http://www.bostonscientific.com/Device.bsci?page=HCP_Overview &navRe1Id=1000.1003&method=D..., accessed Jul. 18, 2008 (4 pages).
J.D. Paulson, M.D., et al., "Development of Flexible Culdoscopy," The Journal of the American Association of Gynecologic Laparoscopists, Nov. 1999, vol. 6, No. 4, pp. 487-490.
H. Seifert, et al., "Retroperitoneal Endoscopic Debridement for Infected Peripancreatic Necrosis," The Lancet, Research Letters, vol. 356, Aug. 19, 2000, pp. 653-655.
K.E. Mönkemüller, M.D., et al., "Transmural Drainage of Pancreatic Fluid Collections Without Electrocautery Using the Seldinger Technique," Gastrointestinal Endoscopy, vol. 48, No. 2, 1998, pp. 195-200, (Received Oct. 3, 1997; Accepted Mar. 31, 1998).
U.S. Appl. No. 12/019,461, filed Jan. 24, 2008.
U.S. Appl. No. 12/045,318, filed Mar. 10, 2008.
U.S. Appl. No. 12/115,916, filed May 6, 2008.
U.S. Appl. No. 12/122,031, filed May 16, 2008.
U.S. Appl. No. 12/129,784, filed May 30, 2008.
U.S. Appl. No. 12/129,880, filed May 30, 2008.
U.S. Appl. No. 12/130,010, filed May 30, 2008.
U.S. Appl. No. 12/130,023, filed May 30, 2008.
U.S. Appl. No. 12/130,224, filed May 30, 2008.

U.S. Appl. No. 12/130,652, filed May 30, 2008.
U.S. Appl. No. 12/133,109, filed Jun. 4, 2008.
U.S. Appl. No. 12/133,953, filed Jun. 5, 2008.
U.S. Appl. No. 12/163,255, filed Jun. 27, 2008.
U.S. Appl. No. 12/169,868, filed Jul. 9, 2008.
U.S. Appl. No. 12/170,862, filed Jul. 10, 2008.
U.S. Appl. No. 12/172,752, filed Jul. 14, 2008.
U.S. Appl. No. 12/172,766, filed Jul. 14, 2008.
U.S. Appl. No. 12/172,782, filed Jul. 14, 2008.
U.S. Appl. No. 12/192,372, filed Aug. 15, 2008.
U.S. Appl. No. 12/203,330, filed Sep. 3, 2008.
U.S. Appl. No. 12/197,749, filed Aug. 25, 2008.
U.S. Appl. No. 12/197,653, filed Aug. 25, 2008.
U.S. Appl. No. 12/202,740, filed Sep. 2, 2008.
U.S. Appl. No. 12/203,458, filed Sep. 3, 2008.
U.S. Appl. No. 12/201,812, filed Aug. 29, 2008.
U.S. Appl. No. 12/207,306, filed Sep. 9, 2008.
U.S. Appl. No. 12/243,334, filed Oct. 1, 2008.
U.S. Appl. No. 12/234,425, filed Sep. 19, 2008.
U.S. Appl. No. 12/060,601, filed Apr. 1, 2008.
U.S. Appl. No. 12/277,975, filed Nov. 25, 2008.
U.S. Appl. No. 12/332,938, filed Dec. 11, 2008.
U.S. Appl. No. 12/337,340, filed Dec. 17, 2008.
U.S. Appl. No. 12/352,451, filed Jan. 12, 2009.
U.S. Appl. No. 12/359,824, filed Jan. 26, 2009.
U.S. Appl. No. 12/352,375, filed Jan. 12, 2009.
U.S. Appl. No. 12/359,053, filed Jan. 23, 2009.
U.S. Appl. No. 12/362,826, filed Jan. 30, 2009.
U.S. Appl. No. 12/363,137, filed Jan. 30, 2009.
U.S. Appl. No. 12/364,172, filed Feb. 2, 2009.
U.S. Appl. No. 12/364,256, filed Feb. 2, 2009.
U.S. Appl. No. 12/413,479, filed Mar. 27, 2009.
U.S. Appl. No. 12/468,462, filed May 19, 2009.
Written Opinion for PCT/US2009/064890, Feb. 3, 2010 (9 pages).
Zadno et al., "Linear Superelasticity in Cold-Worked NI-TI," Engineering Aspects of Shape Memory Alloys, pp. 414-419 (1990).
U.S. Appl. No. 13/013,131, filed Jan. 25, 2011.
U.S. Appl. No. 13/013,147, filed Jan. 25, 2011.
U.S. Appl. No. 12/900,132, filed Oct. 7, 2010.
U.S. Appl. No. 12/939,441, filed Nov. 4, 2010.
U.S. Appl. No. 12/902,531, filed Oct. 12, 2010.
U.S. Appl. No. 12/902,550, filed Oct. 12, 2010.

* cited by examiner

ROTATIONAL COUPLING DEVICE FOR SURGICAL INSTRUMENT WITH FLEXIBLE ACTUATORS

FIELD OF THE INVENTION

The present invention generally relates to methods and devices for controlling movement of a working end of a surgical device.

BACKGROUND

In laparoscopic surgical procedures, a small incision is made in the body and an elongate shaft of a surgical device is inserted through the incision to position a distal end of the shaft at a surgical site. In endoscopic procedures, the elongate shaft of a surgical device is inserted through a natural orifice, such as the mouth or anus, and is advanced along a pathway to position a distal end of the device at a surgical site. Endoscopic procedures typically require the use of a flexible shaft to accommodate the tortuous pathway of the body lumen, whereas rigid shafts can be used in laparoscopic procedures. These tools can be used to engage and/or treat tissue in a number of ways to achieve a diagnostic or therapeutic effect.

Many current laparoscopic and endoscopic devices utilize articulating effectors to provide the user with more control over the orientation of the working end of the instrument. Integration of the controls for articulating, as well as actuating, a working end of a laparoscopic or endoscopic device tend to be complicated by the size constraints of the relatively small pathway through which it is inserted. The controls for an endoscopic device are further complicated by the flexibility of the shaft. Generally, the control motions are all transferred through the shaft as longitudinal translations, which can interfere with the flexibility of the shaft. There is also a desire to lower the force necessary to articulate and/or actuate the working end to a level that all or a great majority of surgeons can handle. One known solution to lower the force-to-fire is to use electrical motors. However, surgeons typically prefer to experience feedback from the working end to assure proper operation of the end effector. The user-feedback effects are not suitably realizable in present motor-driven devices.

U.S. Patent Application Publication No. US 2008/0147113 A1 to Rudolph H. Nobis et al., Ser. No. 11/610,803, filed Dec. 14, 2006, the disclosure of which is herein incorporated by reference in its entirety discloses various manually articulated surgical instruments that may be actuated by manipulating one or more actuation wires that extend from a handle through an elongate tube to an end effector operably coupled to the distal end of the tube. Various embodiments of those devices employ an end effector that may also be selectively rotated relative to a longitudinal axis of the device. When rotated, the actuation wire or wires also rotate to avoid malfunction thereof.

Accordingly, there remains a need for improved rotational coupling arrangement for surgical instruments that are actuated by flexible or semi-flexible members such as wires and the like.

The foregoing discussion is intended only to illustrate some of the shortcomings present in the field of the invention at the time, and should not be taken as a disavowal of claim scope.

BRIEF SUMMARY

Methods and devices are provided for controlling movement of a working end of a surgical device. In one embodiment, a surgical device is provided that has an elongate substantially hollow shaft that defines an elongate axis. An end effector may be operably coupled to a distal end of the elongate shaft for selective pivotal and rotational travel relative thereto. The end effector may have at least one actuation feature thereon that is actuatable upon application of axial actuation motions thereto. An articulation actuator may operably interface with the end effector for applying axial articulation motions thereto to cause the end effector to pivot relative to the distal end of the elongate shaft and selectively apply rotation motions thereto to cause the end effector to rotate relative to the distal end of the elongate shaft about the elongate axis. A first input actuator may be provided for transferring axial actuation motions. Various embodiments further include a rotational coupling that comprises a driving coupler that is movably supported within a portion of the elongate substantially hollow shaft and is also coupled to a distal end of the first input actuator for receiving the axial actuation motions therefrom. An idler coupler may be movably supported within a portion of the substantially elongate hollow shaft and may be rotatably coupled to the driving coupler for rotation relative thereto about the elongate axis. The idler coupler may be further configured for axial travel with the driving coupler along the actuation axis. At least one second input actuator may be coupled to the idler coupler and the actuation features on the end effector such that the second input actuator transfers the axial actuation motions from the rotational coupling to at least one actuation feature of the end effector. A proximal end of a three-bar linkage may be coupled to the distal end of the elongate shaft, and a distal end of the three-bar linkage may be coupled to an end effector. The end effector can be, for example, a grasper, a biopsy probe, a snare loop, forceps, scissors, a needle knife, a sphincterotome, etc. In use, the three-bar linkage is adapted to laterally articulate relative to a longitudinal axis of the elongate shaft to allow the end effector to be angularly oriented relative to the elongate shaft.

In accordance with other embodiments of the present invention, there is provided a surgical device that includes an elongate substantially hollow shaft that defines an elongate axis. An end effector is operably coupled to a distal end of the elongate shaft for selective pivotal and rotational travel relative thereto. The end effector may have at least one actuation feature thereon that is actuatable upon application of at least one axial actuation motion thereto. An articulation actuator may operably interface with the end effector to apply axial articulation motions thereto to cause the end effector to pivot relative to the distal end of the elongate shaft and to selectively apply rotation motions thereto to cause the end effector to rotate relative to the distal end of said elongate shaft about the elongate axis. A first input actuator may extend from the handle assembly to transfer at least one axial actuation motion. The embodiments may further comprise a rotational coupling that has a proximal tubular member that is rotatably supported within the hollow elongate shaft and is coupled to the first input actuator for receiving at least one axial actuation motion therefrom. A distal tubular member may be rotatably supported within the hollow elongate shaft and be coupled to the proximal tubular member for axial travel therewith such that the distal tubular member can rotate relative to the proximal tubular member. At least one second input actuator may be coupled to the distal tubular member and the actuation features on the end effector such that the second input actuator transfers the at least one axial actuation motion applied thereto to at least one actuation feature of the end effector.

In connection with other features of the present invention, there is provided various rotational couplings for surgical devices that are movably coupled to an elongate shaft wherein the surgical device has at least one actuation feature thereon that is actuatable upon application of at least one actuation motion from an actuator and which surgical device is articulatable and rotatable relative to the elongate shaft upon application of other actuation motions from another actuator. Various embodiments of the rotational coupling comprise a driver member that is coupled to the actuator for receiving at least one actuation motion therefrom. An idler member may be rotatably coupled to the driver member for selective rotation relative to the driver member about a longitudinal axis and is configured to axially move as a unit with the driver member. The driver member and the idler member may movably support a portion of the other actuator therein. An output member may be coupled to the idler member and the surgical device for transferring the at least one actuation motion from the idler member to the surgical device.

BRIEF DESCRIPTION OF THE FIGURES

The accompanying drawings, which are incorporated in and constitute a part of this specification, illustrate embodiments of the invention, and, together with the general description of the invention given above, and the detailed description of the embodiments given below, serve to explain the principles of the present invention.

DETAILED DESCRIPTION

Certain exemplary embodiments will now be described to provide an overall understanding of the principles of the structure, function, manufacture, and use of the devices and methods disclosed herein. One or more examples of these embodiments are illustrated in the accompanying drawings. Those of ordinary skill in the art will understand that the devices and methods specifically described herein and illustrated in the accompanying drawings are non-limiting exemplary embodiments and that the scope of the various embodiments of the present invention is defined solely by the claims. The features illustrated or described in connection with one exemplary embodiment may be combined with the features of other embodiments. Such modifications and variations are intended to be included within the scope of the present invention.

The present invention generally provides methods and devices for controlling movement of a working end of a surgical device and, in particular, for performing various surgical procedures using an instrument having an end effector that can be articulated relative to an elongate shaft of the device by means of flexible or semi-flexible actuation members such as, for example, wires. As will described in further detail below, various embodiments are provided with a unique and novel coupling arrangement that permits the end effector to be rotated without adversely affecting the actuation wire or wires. Articulation and rotation of the end effector will allow the end effector to be positioned at various locations during a surgical procedure, thereby providing the user with precise control over the end effector. A person skilled in the art will appreciate that the present invention has application in endoscopic procedures, laparoscopic procedures, and in conventional open surgical procedures, including robotic-assisted surgery.

It will be appreciated that the terms "proximal" and "distal" are used herein with reference to a clinician manipulating the handle portion of the surgical instrument. The term "proximal" referring to the portion closest to the clinician and the term "distal" referring to the portion located away from the clinician. It will be further appreciated that, for convenience and clarity, spatial terms such as "vertical", "horizontal", "up" and "down" may be used herein with respect to the drawings. However, surgical instruments are used in many orientations and positions, and these terms are not intended to be limiting and/or absolute.

Figure 1:
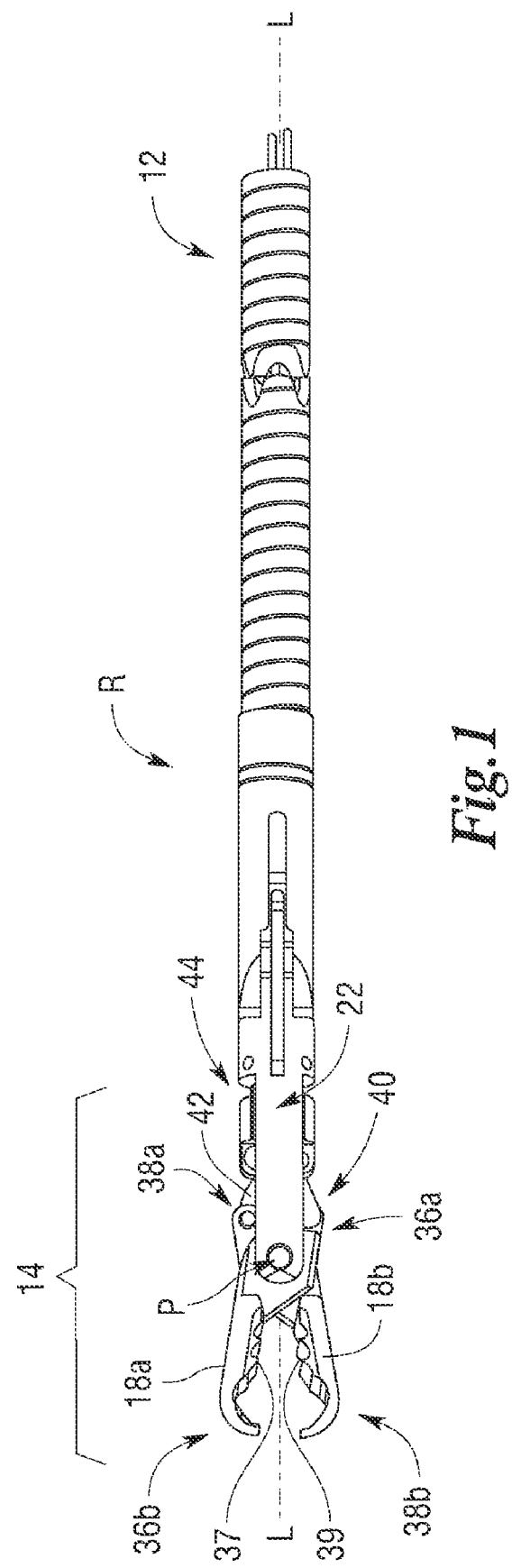
FIG. 1 is a side view of an end effector and portion of elongate shaft with which various rotational coupling embodiments of the present invention may be employed.
Figure 2:
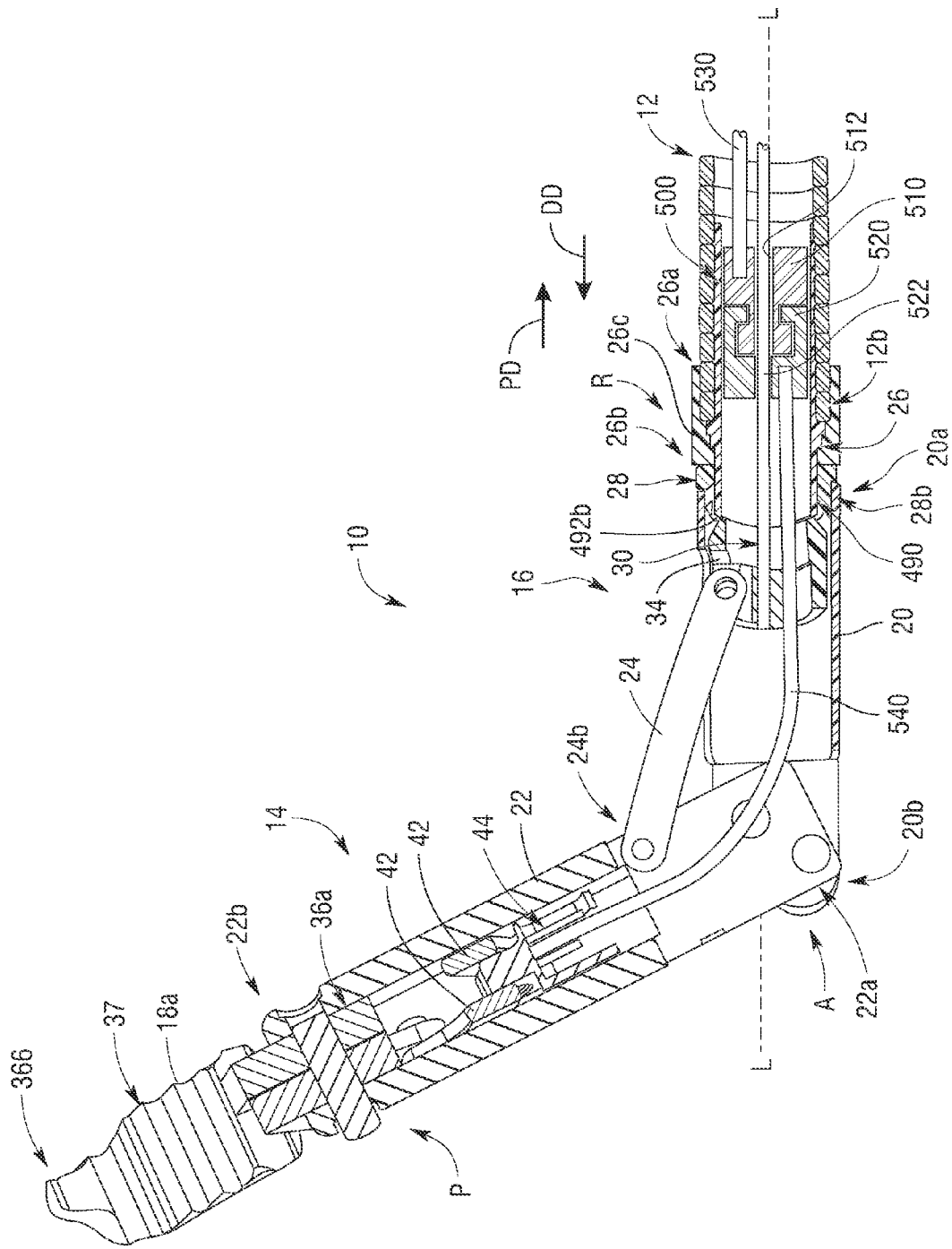
FIG. 2 is a cross-sectional view of the end effector and elongate shaft of FIG. 1 with the end effector shown in an articulated position.

FIGS. 1 and 2 illustrate one exemplary embodiment of an insertion portion 10 of a manually articulatable surgical device. The insertion portion 10 is preferably configured to be inserted into a patient's body, and it can be rigid for laparoscopic applications, flexible for endoscopic applications, or it can have rigid and flexible portions as may be desired. As shown, the insertion portion 10 may include a substantially hollow elongate shaft 12 that has a working end or end effector 14 coupled to a distal end 12b thereof by a three-bar linkage 16. See FIG. 2. While the end effector 14 can have various configurations, as will be discussed in more detail below, in the illustrated embodiment the end effector 14 is in the form of a grasper having "actuation features" such as, for example, opposed jaws 18a, 18b that are pivotally coupled to one another. As used herein, the term "actuation features" refers to movable or otherwise actuatable member(s), device(s), instrument(s), portion(s) of the end effector that are manipulatable or otherwise perform a desired function upon application of one or more actuation motions thereto. Such actuation features may include, but are not limited to, grasper jaws, biopsy forceps, tissue-penetrating spikes, snare loops, scissors, needle knives, sphincterotomes, etc. As the present Detailed Description proceeds, the person of ordinary skill in the art will readily appreciate that the various embodiments of the present invention may be effectively and advantageously employed with a variety of different end effector configurations. Accordingly, the protection afforded to the various embodiments of the present invention should not be limited to a specific end effector that employs a specific actuation feature.

The three-bar linkage 16 allows the end effector 14 to be oriented at an angle relative to a longitudinal axis L-L of the elongate shaft 12. The device can also optionally be configured to allow the end effector 14 to rotate relative to and about the longitudinal axis L-L of the elongate shaft 12. In the illustrated embodiment, the three-bar linkage 16 is rotatably coupled to the distal end 12b of the elongate shaft 12, and thus the three-bar linkage 16, as well as the end effector 14 coupled thereto, can be positioned in various axial orientations. The location of the rotation joint R proximal of the articulation joint A is particularly advantageous in that rotation of the end effector 14 can change the location of the plane within which the end effector 14 articulates.

The three-bar linkage 16 can have a variety of configurations, but in an exemplary embodiment, as shown in more detail in FIG. 2, it includes three links 20, 22, 24 that are movably coupled to one another. Each link can have a variety of configurations, but in an exemplary embodiment, the first and second links 20, 22 each have a generally hollow elongate shape and the third link 24 is in the form of an elongate rod or bar. The first link 20 can have a proximal end 20a that is coupled to a distal end 12b of the elongate shaft 12 via first and second rotation couplings 26 and 28 which will be discussed in more detail below. The distal end 20b of the first link 20 can be movably coupled to a proximal end 22a of the second link 22, e.g., by a pivot joint. The distal end 22b of the second link 22 can in turn be coupled to the end effector 14 for manipulation thereof by the three-bar linkage 16. The third link 24 can extend at least partially through the first and second links 20, 22, and it can have a distal end 24b that is pivotally coupled to the second link 22, e.g., by a pivot pin, to form the three-bar linkage 16. The particular location at which the third link 24 mates to the second link 22 can vary, but it is preferably pivotally mated at a location that will allow the third link 24 to apply a force to the second link 22 to cause the second link 22 to articulate relative to the first link 20. The proximal end of the third link 24 can be coupled to an articulation coupling 34 that is coupled to an articulation actuator 30 that extends through the elongate shaft 12 and at least partially through the first link 20.

The articulation actuator 30 can have a variety of configurations, but in an exemplary embodiment, the articulation actuator 30 comprises a "semi-flexible" member or wire fabricated from, for example, stainless steel, Nickel-Titanium alloy (Nitinol®), etc. As used herein, the term "semi-flexible" means components that are able to exhibit adequate flexibility within the desired strain with pit permanent deformation yet deliver acceptable stiffness for the desired load transmission. As can be seen in FIG. 2, articulation coupling 34 may comprise a tubular member that is attached to the articulation actuator 30 and is pivotally attached to the third link 24. In various embodiments, for example, the articulation actuator 30 may be attached to the articulation coupling 34 by, for example, welding, gluing, swaging, coining, crimping, etc.

In use, proximal movement of the articulation actuator 30 relative to and along the longitudinal axis L-L of the elongate shaft 12 will apply a proximally-directed force to the third link 24. The third link 24 will thus apply a proximally-directed force to the second link 22, causing the second link 22 to pivot laterally relative to the longitudinal axis L-L of the elongate shaft 12. As a result, the second link 22, with the end effector 14 coupled thereto, will move laterally in a single plane to allow the end effector 14 to extend at an angle relative the longitudinal axis L-L of the elongate shaft 12, as shown in FIG. 2. The end effector 14 can be returned to the original, longitudinally-aligned position, shown in FIG. 1 by moving the articulation actuator 30 distally relative to the elongate shaft 12.

Figure 2A:
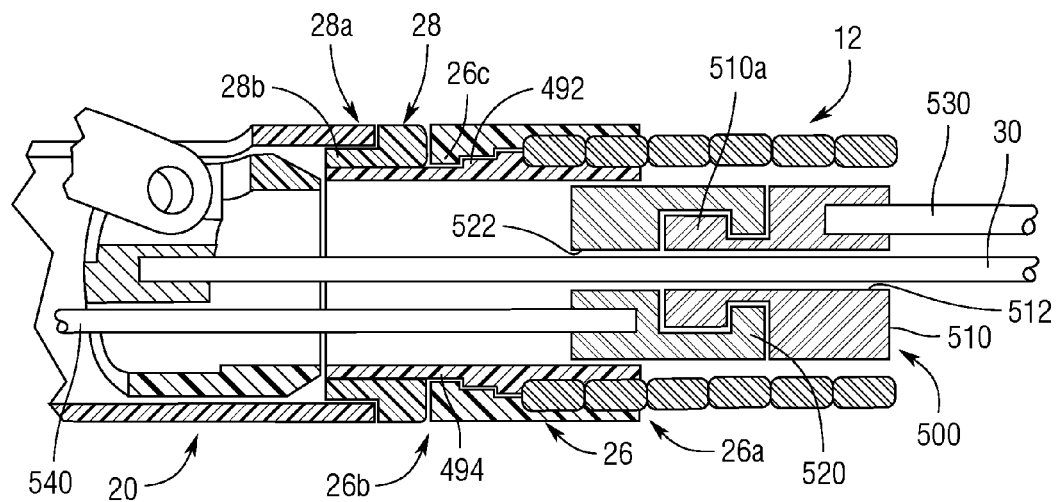
FIG. 2A is an enlarged cross-sectional view of a portion of the end effector of FIG. 2.

As previously indicated, in addition to articulating movement, the end effector 14 can also be configured to rotate relative to the elongate shaft 12, thus allowing the end effector 14 to be positioned in multiple angular orientations. The particular location of the rotation joint R can vary, and it can be located proximal to the three-bar linkage 16, at a mid-portion of the three-bar linkage 16, or distal to the three-bar linkage 16. In an exemplary embodiment, the rotation joint R is located proximal to the three-bar linkage 16, and more preferably proximal to the articulation joint A formed between the first and second links 20, 22. As shown in FIGS. 2 and 2A, the first link 20 can be rotatably coupled to the distal end 12b of the elongate shaft 12 by one or more rotation couplings.

The illustrated embodiment includes first and second rotation couplings 26, 28. Second rotation coupling 28 may be affixed to (e.g., welded, glued, etc.) to a coupling sleeve 490. The first rotation coupling 26 has a generally elongate hollow shape with a proximal end 26a that is fixedly mated to the elongate shaft 12 and a distal end 26b that has deflectable tabs 26c formed therearound. The tabs 26c can be formed by longitudinally-extending cut-outs formed in and spaced radially around the distal end 26b of the first rotation coupling 26. Each tab 26c can include an annular flange or lip formed on an inner surface thereof. The second rotation coupling 28 can be rotatably supported on the coupling sleeve 490 by advancing the tabs 26c over a retention flange 492 on the coupling sleeve 490. The tabs 26c will deflect until the annular flange or lip on the tabs 26c extends into and engages a groove 494 formed in the coupling sleeve 490. The elongate shaft 12 may be affixed to the first rotation coupling 26 by welding, adhesive, etc. Such arrangement permits the first rotation coupling 26 and the elongate shaft 12 to rotate about the coupling sleeve 490.

As can also be seen in FIGS. 2 and 2A, the proximal end 20a of the of first link 20 extends onto the distal end 28b of the second rotation coupling 28, to enable the first link 20 to rotate relative thereto. Rotation of articulation actuator 30 relative to and about the longitudinal axis L-L of the elongate shaft 12 will rotate the articulation coupling 34 and the third link 24, which is coupled to the second link 22, which in turn is coupled to the end effector 14 and the first link 20. As a result, the entire three-bar linkage 16 will rotate with the end effector 14 relative to and about the longitudinal axis L-L of the elongate shaft 12. Rotation can also be done while the end effector 14 is articulated, thereby changing the plane within which the end effector 14 articulates.

Various embodiments of the subject invention may further include a third rotation coupling 500. The third rotation coupling 500 may include a driving coupler 510 that is axially and rotatably movable within the elongate shaft 12 and a portion of the coupling sleeve 490. An idler coupler 520 may be rotatably coupled to a distal end 510a of the driving coupler 510 in the manner depicted in FIGS. 2 and 2A such that the driving coupler 510 and the idler coupler 520 may rotate relative to each other, yet move axially as a unit within the elongate shaft 12. The driving coupler 510 has an axial hole 512 extending therethrough through which a portion of the articulation actuator 30 movably and rotationally extends. Likewise, the idler coupler 520 has an axial hole 522 through which a portion of the articulation actuator 30 movably and rotationally extends. Thus, actuation of the articulation actuator 30 is not impeded by the coupling 500.

Also in various embodiments, a "first" input actuator 530 is attached to the driving coupler 510. The input actuator 530 may comprise, for example, a "semi-flexible" member or wire that may be manufactured from stainless steel, Nickel-Titanium alloy (Nitinol®), etc. Likewise, an output actuator 540 that may comprise, for example, a "semi-flexible" member or wire that may be manufactured from stainless steel, Nickel-Titanium alloy (Nitinol®), etc. is attached to the idler coupler 520 and an actuation pusher 44 in the end effector 14.

As indicated above, the end effector 14 of the device can have various configurations but in the embodiment shown in FIGS. 1 and 2, the end effector 14 is in the form of a grasper having opposed jaws 18a, 18b. Jaw 18a includes a distal portion 36b that may have a series of teeth 37 formed thereon for grasping tissue, and a proximal portion 36a, that pivotally mates to an actuation link 40. See FIG. 1. Jaw 18b includes a distal portion 38b that may have a series of teeth 39 formed thereon for grasping tissue, and a proximal portion 38a that pivotally mates to an actuation link 42. The jaws 18a, 18b may be pivotally mated to one another at a pivot point P located between the proximal and distal portions 36a, 38a, 36b, 38b. The proximal end of each actuation link 40, 42 may be pivotally mated to an actuation pusher 44 that may be slidably disposed within and between opposed slots formed in a distal portion of the second link 22. Such a configuration will prevent independent rotation of the actuation pusher 44 relative to the second link 22. As can also be seen in FIG. 2, the distal end 24b of the second link 24 is pivotally coupled to (pinned) to the link 22.

In use, proximal movement of the input actuator 530 relative to the elongate shaft 12 will pull the driving coupler 510 and idler coupler 520 in the proximal direction "PD" within the coupling sleeve 490. Movement of the idler coupler 520 in the proximal direction "PD" also causes the actuation pusher 44 to move within the slots formed in the second link 22. The actuation links 40, 42 will thus be pulled in the proximal direction "PD", bringing the proximal and distal portions 36a, 38a, 36b, 38b of each jaw 18a, 18b toward each other to thereby close the jaws 18a, 18b. Conversely, distal movement of the input actuator 530 causes the driving coupler 510 and idler coupler 520 to move distally and cause the actuation pusher 44 to also move distally within the slots formed in the second link 22. Such movement will cause the links 40, 42 and the proximal and distal portions 36a, 38a, 36b, 38b of the jaws 18a, 18b to pivot laterally outward, thereby opening the jaws 18a, 18b.

Figure 3:
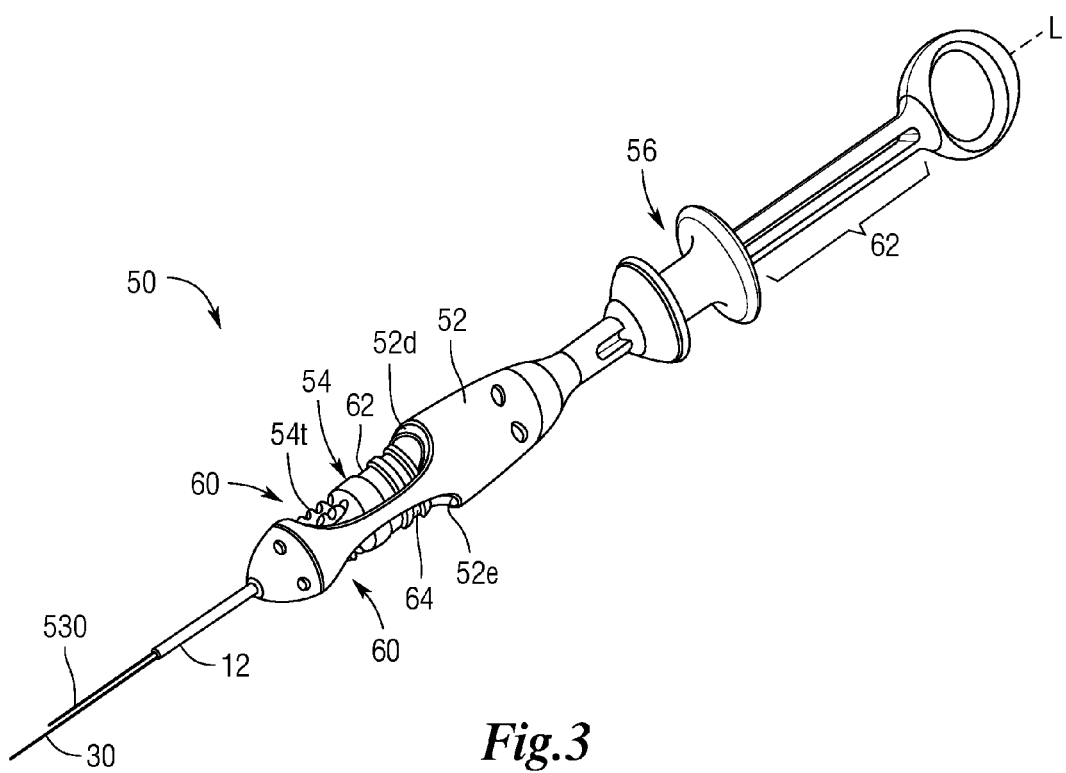
FIG. 3 is a perspective view of a handle assembly embodiment that may be employed in connection with various embodiments of the present invention.
Figure 4:
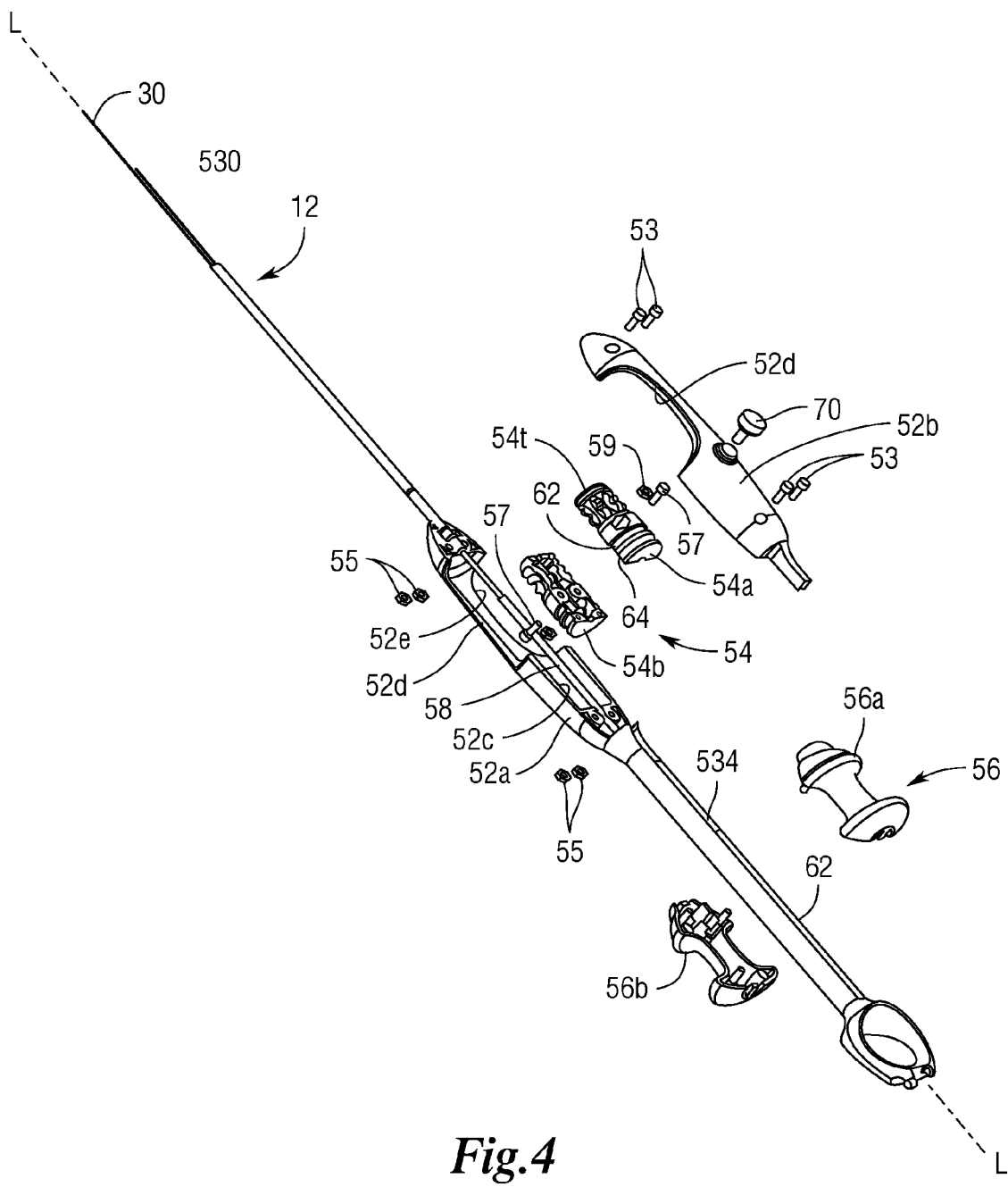
FIG. 4 is an exploded assembly view of the handle assembly of FIG. 3.
Figure 5:
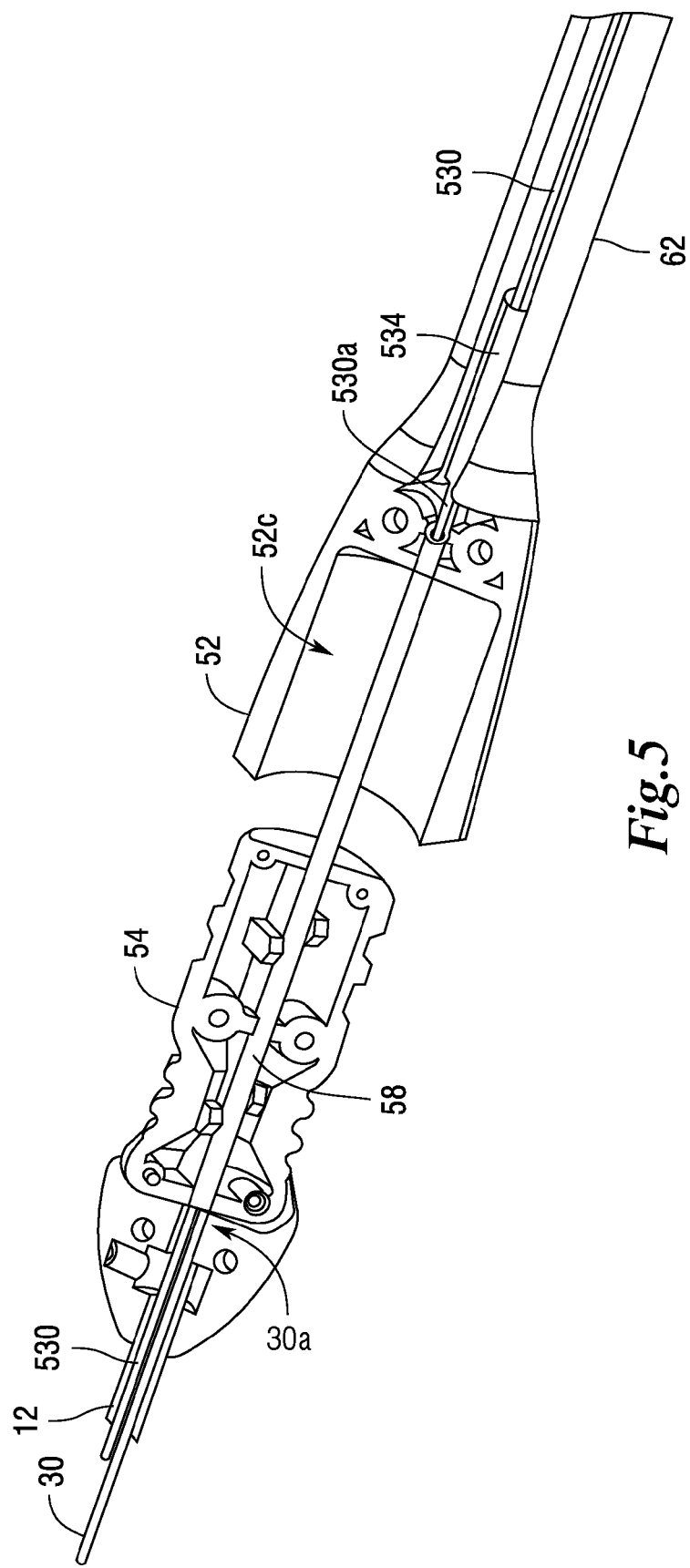
FIG. 5 is a partial assembly view of a portion of the handle assembly of FIGS. 3 and 4.
Figure 6:
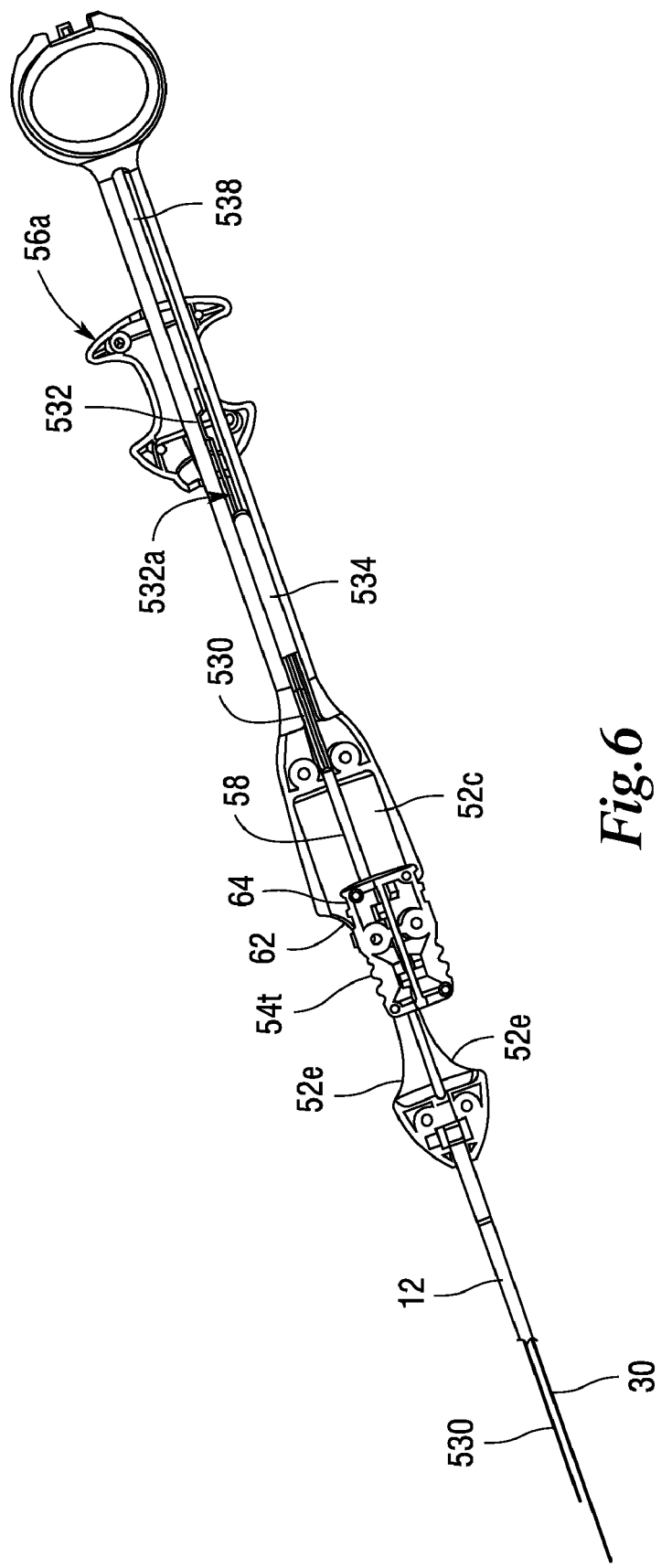
FIG. 6 is another partial assembly view of a portion of the handle assembly of FIGS. 3-5.

As previously indicated, the device can also include a handle assembly 50 coupled to the proximal end of the elongate shaft 12 and have various controls formed thereon for controlling and manipulating the device. A person skilled in the art will appreciate that the particular configuration of the handle can vary, and that various techniques known in the art can be used for effecting movement of various portions on the device. FIGS. 3-5 illustrate one exemplary embodiment of a handle 50 for use with the insertion portion 10 of the device shown in FIGS. 1 and 2. As shown, the handle 50 has a generally elongate cylindrical configuration to facilitate grasping thereof. The handle housing 52 can have an integral or unitary configuration, or it can be formed from two housing halves 52a, 52b that mate together to enclose various components therein. The housing halves 52a, 52b are shown in FIG. 4 and may be removably attached together by bolts 53 and nuts 55. The various components disposed within the handle housing 52 can also vary, but in an exemplary embodiment, the handle assembly 50 includes an articulation knob 54 for articulating and rotating the end effector 14, and an actuation knob 56 for actuating the end effector 14.

The articulation knob 54 may have a generally cylindrical configuration. The knob 54 can have an integral or unitary configuration, or it can be formed from two halves 54a, 54b that may be coupled together by bolts 57 and nuts 59, as shown. While various techniques can be used to affix the articulation actuator 30 to the articulation knob 54, in an exemplary embodiment the articulation knob 54 includes an axle 58 fixedly disposed therein and engaged between the knob halves 54a, 54b. The articulation actuator 30 extends through an inner lumen of the axle 58 and is affixed thereto. Various fastening techniques can be used to affix the articulation actuator 30 to the axle 58 including, for example, an interference or compression fit, an adhesive, or other mechanical or chemical mating techniques known in the art. The proximal end 30a of the articulation actuator 30 can mate to the knob 54 such that rotation and translation of the knob 54 will cause corresponding rotation and translation of the articulation actuator 30, thereby rotating and articulating the end effector 14, as previously described.

In various embodiments, the handle housing 52 can include an elongate cavity 52c formed therein that is configured to slidably and rotatably receive a portion of the knob 54 therein. The handle housing 52 can also include one or more cut-outs 60 formed therein for allowing a user to access the knob. FIG. 3 illustrates opposed cut-outs 52d, 52e formed in the handle housing 52. The articulation knob 54 can also include features to facilitate movement thereof. For example, the articulation knob 54 can include one or more surface features formed on an external surface thereof for allowing the user to more easily grasp the knob. In the illustrated embodiment, the knob 54 includes a series of longitudinally-oriented teeth 54t formed on a portion thereof. In various embodiments, the articulation knob 54 may have two axially spaced annular grooves 62 and 64 formed therein as shown. In particular, when the articulation knob 54 has been moved to its distal-most position, the annular groove 62 is positioned to selectively receive a locking screw 70 therein. Likewise, when the articulation knob 54 is in its proximal-most position, the annular groove 64 is positioned to selectively receive the locking screw 70 therein. Thus, by use of the locking screw 70, the surgeon may lock the device in a desired articulated position.

In use, the articulation knob 54 can be grasped by a user and rotated about its longitudinal axis (i.e., about the longitudinal axis L-L of the shaft 12 and handle 50). Rotation of the knob 54 will cause corresponding rotation of the axle 58 and the articulation actuator 30. The articulation actuator 30 is not coupled to the articulation knob 54 and therefore is not affected by its actuation. As previously explained, rotation of the articulation actuator 30 will cause corresponding rotation of the three-bar linkage 16 and the end effector 14. The articulation knob 54 can also be moved or translated longitudinally along the longitudinal axis L-L, and within the elongate cavity 52c formed in the handle housing 52. Proximal movement of the articulation knob 54 within the handle housing 52 will pull the articulation actuator 30 in the proximal direction "PD", thereby articulating the end effector 14, as previously explained. Distal movement of the articulation knob 54 within the handle housing 52 will in turn move the articulation actuator 30 distally, thereby returning the end effector 14 to its original longitudinally-aligned position.

As indicated above, the device can also include an actuation knob 56 for actuating the actuation features on the end effector 14 (i.e. for firing, opening and closing, energizing, etc.). The actuation knob 56 can have a variety of configurations, but in the illustrated embodiment the knob 56 has a bar-bell shape. The knob 56 can have an integral or unitary configuration, or it can be formed from two halves 56a, 56b that mate together, as shown in FIG. 4. The proximal end 530a of the input actuator 530 can be affixed to the actuation knob 56 such that translation of the knob 56 will cause corresponding translation of the input actuator 530, thereby actuating the end effector 14 as previously described. In the illustrated embodiment, the proximal end 530a of the input actuator 530 may have a bend 532 formed therein for mating with the actuation knob 56 as described, for example, in U.S. Patent Publication No. U.S. 2008/0147113 A1, which has been herein incorporated by reference in its entirety. The proximal end 530a may be slidably supported within a support member 534 that is slidably received within a slot 538 formed in a shaft portion 62 of the handle 60. The input actuator 530 also passes through the axle 58 such that it may axially slide therein and axle 58 may be freely rotated therearound.

Actuation knob 56 is slidably disposed around an elongate shaft portion 62 of the handle housing 52. In use, the knob 56 can be grasped by a user and translated along the shaft portion 62 of the handle housing 52. Proximal movement of the actuation knob 56 along the shaft portion 62 will pull the input actuator 530 proximally, thereby opening the jaws 18a, 18b of the end effector 12 as previously explained. Distal movement of the actuation knob 56 along the shaft portion 62 will in turn move the input actuator 530 distally, thereby moving the jaws 18a, 18b to the closed position. Those of ordinary skill in the art will appreciate that the unique and novel third rotational coupler 500 of the present invention enables the actuators 30, 530, 540 to be independently operated while avoiding aberrant twisting/jamming of the actuators when the end effector is to be articulated, rotated and/or actuated.

Figure 7:
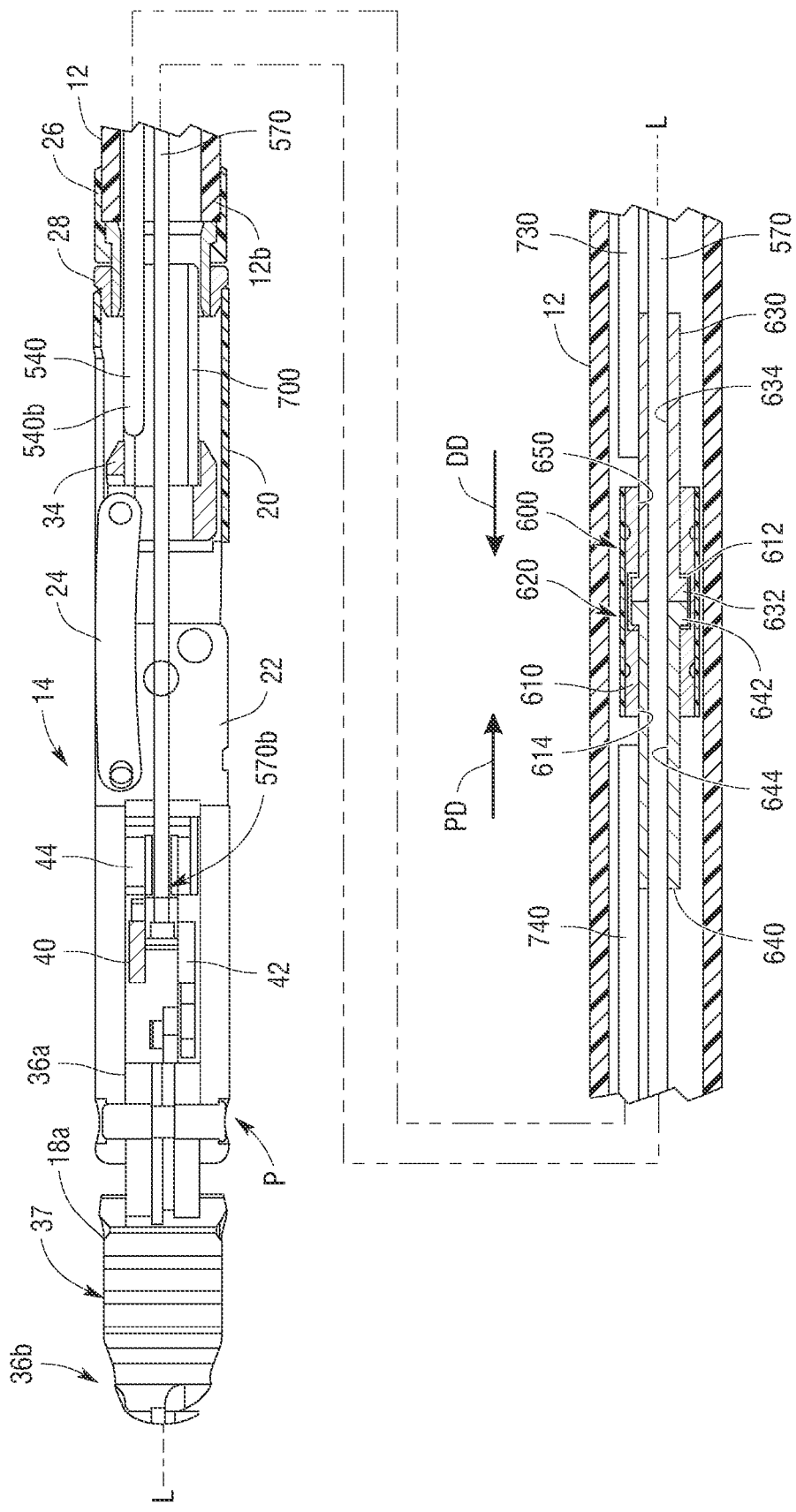
FIG. 7 is a cross-sectional view of another end effector and elongate shaft employing another rotational coupling embodiment of the present invention.

Another rotational coupler embodiment 600 of the present invention is depicted in FIG. 7. As can be seen in that Figure, the rotational coupler 600 may include a coupler housing 610 that is supported in an outer sheath 620 which is supported in the hollow elongate shaft 12. The coupling housing 610 may be fabricated from, for example, stainless steel, etc. and be provided in two mating pieces that may be coupled together by welding, gluing, swaging, coining, crimping, etc. The outer sheath 620 may be fabricated from, for example, stainless steel, etc. In various embodiments, the coupling housing 610 has a centrally disposed cylindrical opening 612 formed therein and an axial passage 614 extending therethrough. A proximal tubular member 630 that has a flanged end 632 is mounted within the coupling housing 610 as shown. Likewise, a distal tubular member 640 that has a flanged end 642 is also mounted within the coupling housing 610 as shown. Tubular members 630, 640 may be fabricated from, for example, stainless steel, etc. Tubular members 630, 640 are sized to axially rotate about axis L-L relative to the coupling housing 610 as will be discussed in further detail below.

As can be further seen in FIG. 7, the proximal tubular member 630 has an axial passage 634 therethrough and the distal tubular member 640 has a passage 644 therethrough. When mounted within the coupling housing 610, the passages 634 and 644 are coaxially aligned to form a passage 650 through the coupler for operably receiving an actuator member 570 therethrough such that the actuation member 570 can freely move axially and rotate within the passage 650. The actuation member 570 may comprise, for example, stainless steel, Nickel-Titanium alloy (Nitinol®), etc. The device may have a handle member of the type described above such that the proximal end of the actuation member 570 is coupled to the actuation knob 56 in the manners described above. The distal end 570b of the actuation member 570 may be coupled to the actuation pusher 44 in the above-described manner. In use, proximal movement of the actuation member 570 relative to the elongate shaft 12 will pull the actuation pusher 44 in the proximal direction "PD" within the slots formed in the second link 22. The actuation links 40, 42 will thus be pulled proximally "PD", bringing the proximal and distal portions 36a, 38a, 36b, 38b of each jaw 18a, 18b toward each other to thereby close the jaws 18a, 18b. Conversely, distal movement of the actuation member 570 causes the actuation pusher 44 to also move distally within the slots formed in the second link 22, which will cause the links 40, 42 and the proximal and distal portions 36a, 38a, 36b, 38b of the jaws 18a, 18b to pivot laterally outward, thereby opening the jaws 18a, 18b.

Also in various embodiments, an input articulation member 730 is non-movably affixed to the proximal end of the proximal tubular member 630. The input articulation member 730 may comprise, for example, stainless steel, Nickel-Titanium alloy (Nitinol®), etc. and be non-movably affixed to the proximal tubular member 630 by, for example, welding, gluing, swaging, coining, crimping, etc. The proximal end of the input articulation member 730 may be coupled to the articulation knob 54 in the manners described above. Thus, the input articulation member 730 may be axially and rotatably moved within the elongate shaft 12 by manipulation of the articulation knob 54.

Also in various embodiments, an output articulation member 740 is non-movably attached to the distal tubular member 640 and the articulation coupling 34. The output articulation member 740 may comprise, for example, stainless steel, Nickel-Titanium alloy (Nitinol®), etc. and be attached to the distal tubular member 640 by, for example, welding, gluing, swaging, coining, crimping, etc. In use, movement of the input articulation member 730 in the proximal direction "PD" relative to and along the longitudinal axis L-L of the elongate shaft 12 will pull the proximal tubular member 630 as well as the entire rotational coupler 600 in the proximal direction "PD" and will apply a proximally-directed force to the third link 24. The third link 24 will thus apply a proximally-directed force to the second link 22, causing the second link 22 to pivot laterally relative to the longitudinal axis L-L of the elongate shaft 12. As a result, the second link 22, with the end effector 14 coupled thereto, will move laterally in a single plane to allow the end effector 14 to extend at an angle relative the longitudinal axis L-L of the elongate shaft 12. The end effector 14 can be returned to the original, longitudinally-aligned position, shown in FIG. 1 by moving the input articulation member 730 distally relative to the elongate shaft 12.

Rotation of input articulation member 730 relative to and about the longitudinal axis L-L of the elongate shaft 12 will rotate the articulation coupling 34 and the third link 24, which is coupled to the second link 22, which in turn is coupled to the end effector 14 and the first link 20. As a result, the entire three-bar linkage 16 will rotate with the end effector 14 relative to and about the longitudinal axis L-L of the elongate shaft 12. Rotation can also be accomplished while the end effector 14 is articulated, thereby changing the plane within which the end effector 14 articulates. Again such unique and novel rotational coupler arrangement enable the actuators 30, 530, 540 to be independently operated while avoiding aberrant twisting/jamming of the actuators when the end effector is to be articulated, rotated and/or actuated.

While the rotational couplers discussed above are described and shown in connection with an end effector that employs actuation features such as grasper jaws, the various coupler embodiments of the present invention may be effectively employed in connection with a variety of other end effectors for performing various surgical procedures. Examples of such end effector arrangements may comprise those end effector arrangements described in U.S. Patent Application Publication No. U.S. 2008/0147113, such as, for example, biopsy forceps, tissue-penetrating spikes, snare loops, scissors, needle knives and sphincterotomes. A person skilled in the art will appreciate that the rotation coupler embodiments of the present invention may be used in connection with a variety of other end effectors other than those described and illustrated herein and in the aforementioned published application which has been herein incorporated by reference in its entirety.

As indicated above, the various devices disclosed herein for controlling movement of a working end of a surgical device can be used in a variety of surgical procedures, including endoscopic procedures, laparoscopic procedures, and in conventional open surgical procedures, including robotic-assisted surgery. In one exemplary endoscopic procedure, an elongate shaft of a surgical device, such as one previously disclosed herein, can be inserted through a natural orifice and a body lumen to position an end effector located at a distal end of the elongate shaft adjacent to tissue to be treated. An articulation actuator can be translated along a longitudinal axis of the elongate shaft to cause a three-bar linkage to laterally articulate the end effector in a direction substantially perpendicular to a longitudinal axis of the elongate shaft to allow the end effector to be angularly oriented relative to the elongate shaft. This can be achieved by actuating one or more actuation mechanisms formed on a handle of the device. The method can also include rotating the end effector relative to the elongate shaft. In one embodiment, the three-bar linkage can rotate with the end effector relative to the elongate shaft. For example, the articulation actuator can be rotated relative to the elongate shaft to rotate both the three-bar linkage and the end effector. In another embodiment, the end effector can rotate relative to the three-bar linkage. For example, an actuation wire coupled to the end effector and extending through the elongate shaft and the three-bar linkage can be rotated.

The devices disclosed herein can be designed to be disposed of after a single use, or they can be designed to be used multiple times. In either case, however, the device can be reconditioned for reuse after at least one use. Reconditioning can include any combination of the steps of disassembly of the device, followed by cleaning or replacement of particular pieces, and subsequent reassembly. In particular, the device can be disassembled, and any number of the particular pieces or parts of the device can be selectively replaced or removed in any combination. Upon cleaning and/or replacement of particular parts, the device can be reassembled for subsequent use either at a reconditioning facility, or by a surgical team immediately prior to a surgical procedure. Those skilled in the art will appreciate that reconditioning of a device can utilize a variety of techniques for disassembly, cleaning/replacement, and reassembly. Use of such techniques, and the resulting reconditioned device, are all within the scope of the present application.

Preferably, the invention described herein will be processed before surgery. First, a new or used instrument is obtained and if necessary cleaned. The instrument can then be sterilized. In one sterilization technique, the instrument is placed in a closed and sealed container, such as a plastic or TYVEK bag. The container and instrument are then placed in a field of radiation that can penetrate the container, such as gamma radiation, x-rays, or high-energy electrons. The radiation kills bacteria on the instrument and in the container. The sterilized instrument can then be stored in the sterile container. The sealed container keeps the instrument sterile until it is opened in the medical facility.

It is preferred that device is sterilized. This can be done by any number of ways known to those skilled in the art including beta or gamma radiation, ethylene oxide, steam.

Any patent, publication, or other disclosure material, in whole or in part, that is said to be incorporated by reference herein is incorporated herein only to the extent that the incorporated materials does not conflict with existing definitions, statements, or other disclosure material set forth in this disclosure. As such, and to the extent necessary, the disclosure as explicitly set forth herein supersedes any conflicting material incorporated herein by reference. Any material, or portion thereof, that is said to be incorporated by reference herein, but which conflicts with existing definitions, statements, or other disclosure material set forth herein will only be incorporated to the extent that no conflict arises between that incorporated material and the existing disclosure material.

The invention which is intended to be protected is not to be construed as limited to the particular embodiments disclosed. The embodiments are therefore to be regarded as illustrative rather than restrictive. Variations and changes may be made by others without departing from the spirit of the present invention. Accordingly, it is expressly intended that all such equivalents, variations and changes which fall within the spirit and scope of the present invention as defined in the claims be embraced thereby.

What is claimed is:

1. A surgical device, comprising:
an elongate substantially hollow shaft defining an elongate axis;
an end effector operably coupled to a distal end of said elongate shaft for selective pivotal and rotational travel relative thereto, said end effector having at least one actuation feature thereon that is actuatable upon application of at least one axial actuation motion thereto;
an articulation actuator operably interfacing with said end effector for applying at least one axial motion thereto to cause said end effector to pivot relative to said distal end of said elongate shaft and for selectively applying at least one rotation motion thereto to cause said end effector to rotate relative to said distal end of said elongate shaft about said elongate axis;
a rotational coupling, comprising:
a driving coupler movably supported within a portion of said elongate substantially hollow shaft; and
an idler coupler movably supported within said portion of said substantially elongate hollow shaft and rotatably coupled to said driving coupler for rotation relative thereto about said elongate axis and axial travel with said driving coupler along said actuation axis;
an input actuator for applying said at least one axial actuation motion, said input actuator coupled at a distal end to the driving coupler, wherein said at least one axial actuation motion is transmitted to said driving coupler, and wherein said driving coupler transmits said at least one axial actuation motion to said idler coupler; and
at least one output actuator coupled at a proximal end to said idler coupler and at a distal end to said actuation features on said end effector such that said output actuator transfers said at least one axial actuation motion from said rotational coupling to said at least one actuation feature of said end effector.

2. The surgical device of claim 1 wherein said actuation feature is selected from the group of actuation features consisting of grasper jaws, a biopsy probe, a snare loop, forceps, scissors, a needle knife, and a sphincterotome.

3. The surgical device of claim 1 wherein said articulation actuator comprises a semi-flexible wire that is axially and rotatably movable relative thereto.

4. The surgical device of claim 1 wherein said input actuator comprises a first semi-flexible wire and wherein said output actuator comprises a second semi-flexible wire.

5. The surgical device of claim 1 wherein said end effector is operably coupled to said distal end of said substantially hollow elongate shaft by a multiple-bar linkage.

6. The surgical device of claim 5 wherein said multiple-bar linkage comprises:
a first substantially hollow link rotatably coupled at a proximal end to said distal end of said substantially hollow elongate shaft and such that said first link may rotate about said elongate axis, wherein said rotation causes said end effector to rotate about said elongate axis, and wherein the first substantially hollow link is pivotably coupled to said end effector such that said end effector may pivot relative thereto about a pivot axis;

a second link coupled to said articulation actuator and movably supported within said first link for axial travel relative thereto in response to said axial articulation motions applied thereto from said articulation actuator; and a third link pivotally coupled to said first link and to said second link and coupled to said end effector such that the application of said axial articulation motions to said second link by said articulation actuator causes said end effector to pivot about said pivot axis.

7. The surgical device of claim 1 further comprising a handle assembly coupled to a proximal end of said substantially hollow elongate shaft.

8. The surgical device of claim 7 wherein said articulation actuator is operably coupled to an articulation knob that is rotatably and axially movably supported on said handle assembly and wherein said input actuator is operably coupled to an actuation knob that is axially movably supported on said handle assembly.

9. The surgical device of claim 1 wherein the end effector is operably coupled to said distal end of said elongate shaft by a second rotation coupling, wherein said second rotation coupling includes a first portion that is fixedly coupled at a proximal end to said elongate shaft and includes a second portion that is fixedly coupled at a distal end to said end effector, and wherein a proximal end of the second portion is rotatably coupled to a distal end of the first portion for rotation thereto.

10. The surgical device of claim 9 wherein said articulation actuator passes through an opening in said first rotational coupling and an opening in said second rotation coupling.

11. The surgical device of claim 9 wherein said end effector is operably coupled to said distal end of said second portion of said second rotation coupling by a multiple-bar linkage comprising:

a first substantially hollow link rotatably coupled at a proximal end to said distal end of said second portion of said second rotation coupling such that said first link may rotate about said elongate axis, wherein rotation causes said end effector to rotate about said elongate axis, and wherein the first substantially hollow link is pivotably coupled to said end effector such that said end effector may pivot relative thereto about a pivot axis;

a second link coupled to said articulation actuator and movably supported within said first link for axial travel relative thereto in response to said axial articulation motions applied thereto from said articulation actuator; and a third link pivotally coupled to said first link and to said second link and coupled to said end effector such that application of said axial articulation motions to said second link by said articulation actuator causes said end effector to pivot about said pivot axis.

12. A surgical device, comprising:

an elongate substantially hollow shaft defining an elongate axis;

an end effector operably coupled to a distal end of said elongate shaft for selective pivoting relative to the elongate axis and rotating about the elongate axis, said end effector having at least one actuation feature thereon that is actuatable upon application of at least one axial actuation motion thereto;

an articulation actuator operably interfacing with said end effector and configured to move along the elongate axis and to rotate about the elongate axis, wherein motion of the articulation actuator along the elongate axis causes said end effector to pivot relative to the elongate axis, and wherein rotation of the articulation actuator about the elongate axis causes the end effector to rotate about the elongate axis;

an input actuator coupled to the articulation actuator, wherein the input actuator transmits force to the articulation actuator in a direction along the elongate axis and transmits torque to the articulation actuator about the elongate axis; and a rotational coupling comprising:

a driving coupler arranged within a portion of the elongate substantially hollow shaft, wherein the driving coupler is movable along the elongate axis within the portion of the elongate substantially hollow shaft, and wherein the driver coupler is fixed relative to the elongate axis;

an idler coupler arranged within the portion of the elongate substantially hollow shaft and rotatably coupled to the driving coupler, wherein the idler coupler is movable along the elongate axis and with the driving coupler, and wherein the idler coupler rotates about the elongate axis; and an output actuator coupled at a proximal end to the idler coupler and at a distal end to the end effector, the output actuator applying the at least one axial actuation motion to the at least one actuation feature of the end effector when the driving coupler and the idler coupler move along the elongate axis.

* * * * *